(12) United States Patent
Bosch et al.

(10) Patent No.: US 7,695,627 B2
(45) Date of Patent: Apr. 13, 2010

(54) TANGENTIAL FLOW FILTRATION DEVICES AND METHODS FOR LEUKOCYTE ENRICHMENT

(75) Inventors: Marnix L. Bosch, Medina, WA (US); Paul C. Harris, Bothell, WA (US); Steven J. Monahan, Kenmore, WA (US); Allen Turner, Seattle, WA (US); Alton L. Boynton, Kingston, WA (US); Patricia A. Lodge, Everett, WA (US)

(73) Assignee: Northwest Biotherapeutics, Inc., Bethesda, MD (US)

( * ) Notice: Subject to any disclaimer, the term of this patent is extended or adjusted under 35 U.S.C. 154(b) by 1166 days.

(21) Appl. No.: 10/517,871

(22) PCT Filed: Jun. 19, 2003

(86) PCT No.: PCT/US03/19428

§ 371 (c)(1),
(2), (4) Date: Dec. 13, 2004

(87) PCT Pub. No.: WO04/000444

PCT Pub. Date: Dec. 31, 2003

(65) Prior Publication Data

US 2005/0173315 A1    Aug. 11, 2005

Related U.S. Application Data

(60) Provisional application No. 60/390,730, filed on Jun. 19, 2002.

(51) Int. Cl.
*B01D 61/20* (2006.01)

(52) U.S. Cl. ............... 210/645; 210/137; 210/195.2; 210/321.6; 210/321.87; 210/651; 210/805; 422/101; 436/178; 435/286.5; 435/297.1; 435/404

(58) Field of Classification Search .............. 210/137, 210/195.1, 195.2, 321.6, 321.65, 637, 641, 210/645, 650, 651, 652, 805, 806, 321.87; 435/7.1, 7.24, 286.5, 288.5, 288.6, 288.7, 435/289.1, 297.1, 304.1, 372, 404; 422/101; 436/178; 424/93.7, 534, 577
See application file for complete search history.

(56) References Cited

U.S. PATENT DOCUMENTS 4,191,182 A    3/1980    Popovich et al.

(Continued)

FOREIGN PATENT DOCUMENTS

EP    0 208 450 A2    1/1987

(Continued)

OTHER PUBLICATIONS

Yamanishi et al U.S. Appl. No. 60/394,517, filed Jul. 9, 2002.*

(Continued)

*Primary Examiner*—Joseph W Drodge
(74) *Attorney, Agent, or Firm*—Townsend and Townsend and Crew, LLP

(57) ABSTRACT

The present invention provides tangential flow filtration devices and methods for enriching a heterogeneous mixture of blood constituents for leukocytes by removal of non-leukocyte blood constituents. In one particular embodiment the device can provide a composition enriched in monocytes. One embodiment includes a remover unit (1) having a cross-flow chamber (3) separated by a microporous filter (5) from a filtrate chamber (4), the remover unit (1) also having a tangential flow inlet (6), a fluid outlet (7) for a fluid enriched in leukocytes and a filtrate outlet (8).

45 Claims, 11 Drawing Sheets

U.S. PATENT DOCUMENTS

| | | | |
|---|---|---|---|
| 4,411,792 A | | 10/1983 | Babb |
| 4,420,398 A | | 12/1983 | Castino |
| 4,644,056 A | | 2/1987 | Kothe et al. |
| 4,722,902 A | * | 2/1988 | Harm et al. ............... 435/297.4 |
| 4,751,003 A | * | 6/1988 | Raehse et al. ................ 210/639 |
| 4,753,733 A | | 6/1988 | Ramstack et al. |
| 5,026,365 A | * | 6/1991 | Rossini et al. ........... 604/891.1 |
| 5,423,738 A | | 6/1995 | Robinson et al. |
| 5,601,727 A | | 2/1997 | Bormann et al. |
| 5,690,815 A | | 11/1997 | Krasnoff et al. |
| 5,695,653 A | * | 12/1997 | Gsell et al. .................. 210/767 |
| 5,744,047 A | | 4/1998 | Gsell et al. |
| 5,788,963 A | | 8/1998 | Murphy et al. |
| 5,922,210 A | * | 7/1999 | Brody et al. ................ 210/767 |
| 5,948,441 A | | 9/1999 | Lenk et al. |
| 6,045,546 A | | 4/2000 | Drago et al. |
| 6,168,718 B1 | | 1/2001 | Sutter et al. |
| 6,194,204 B1 | | 2/2001 | Crawford et al. |
| 6,214,221 B1 | * | 4/2001 | Kopf ....................... 210/198.2 |
| 6,322,709 B1 | | 11/2001 | Krasnoff et al. |
| 6,398,956 B1 | | 6/2002 | Coville et al. |
| 6,491,819 B2 | * | 12/2002 | Prince et al. ........... 210/321.67 |
| 6,495,037 B1 | | 12/2002 | Schuyler et al. |
| 6,497,821 B1 | | 12/2002 | Bellamy, Jr. |
| 6,544,751 B1 | | 4/2003 | Brandwein et al. |
| 6,949,355 B2 | * | 9/2005 | Yamanishi et al. ............ 435/34 |
| 2003/0134416 A1 | * | 7/2003 | Yamanishi et al. .......... 435/372 |

FOREIGN PATENT DOCUMENTS

| | | |
|---|---|---|
| EP | 0 834 329 A1 | 4/1998 |
| JP | 2000217908 | 8/2000 |
| RU | 2056866 C1 | 6/1992 |
| RU | 2113863 | 5/1995 |
| WO | WO 85/03011 | 7/1985 |
| WO | WO 97/03186 | 1/1997 |
| WO | WO 98/13131 | 4/1998 |
| WO | WO 01/09288 A1 | 2/2001 |

OTHER PUBLICATIONS

Yamanishi et al U.S. Appl. No. 60/348,228, filed Oct. 29, 2001.*

Yaminishi et al U.S. Appl. No. 60/328,774, filed Oct. 11, 2001.*

Bacigalupo et al., "Bone Marrow or Peripheral Blood as a Source of Stem Cells for Allogeneic Transplantation," *Haematologica* 87:4-8 (2002).

DeBoer et al., "Changes in L-selectin Expression on CD34-positive Cells Upon Cryopreservation of Peripheral Blood Stem Cell Transplants," *Bone Marrow Transplant.* 22:1103-1110 (1998).

Genovesi, "Several Uses for Tangential-flow Filtration in the Pharmaceutical Industry," *J. Parenter. Aci. Technol.* 37:81-86 (1983).

Quirk and Woodrow, "Investigation of the Parameters Affecting the Separation of Bacterial Enzymes From Cell Debris by Tangential Flow Filtration," *Enzyme Microb. Technol.* 6:201-206 (1984).

Radlett, "The Concentration of Mammalian Cells in a Tangential Flow Filtration Unit," *J. Appl. Chem. Biotechnol.* 22:495-499 (1972).

Rowley et al., "Isolation of CD34+ Cells From Blood Stem Cell Components Using the Baxter Isolex System," *Bone Marrow Transplant.* 21:1253-1262 (1998).

* cited by examiner

TANGENTIAL FLOW FILTRATION DEVICES AND METHODS FOR LEUKOCYTE ENRICHMENT

CROSS REFERENCES TO RELATED APPLICATIONS

This is a U.S. National Stage Application under 35 U.S.C. §371 of International Application No. PCT/US03/19428, filed on Jun. 19, 2003 which claims priority to United States provisional patent application Ser. No. 60/390,730, filed Jun. 19, 2002, which is incorporated herein by reference in its entirety.

BACKGROUND OF THE INVENTION

Blood cell populations enriched for leukocytes are often desired for use in research or therapy. Typical sources of leukocytes include whole peripheral blood, leukopheresis or apheresis product, or other less common sources, such as umbilical cord blood. Enrichment of leukocytes can be done in several ways. Typical methods include density step gradients (e.g., FICOLL-HYPAQUE®, colloidal silica, and the like), elutriation, centrifugation, lysis of erythrocytes by hypotonic shock, and various combinations of these methods. There are disadvantages to each of these methods, one of which is the need for laborious washing steps after the enrichment step is performed.

Following enrichment, the cells are typically washed by a repetitive process. The steps generally include placing the enriched cell suspension into a centrifuge tube and pelleting the cells to the bottom of the tube by use of a centrifuge. The tube is removed from the centrifuge, and the supernatant is decanted from the pelleted cells. A wash liquid is added to the tube, and the cell pellet is resuspended. These steps are typically repeated 2 to 4 times.

One disadvantage of this washing process is that sequential resuspension and centrifugation can decrease cell viability and increase cell lysis. Another disadvantage of washing by centrifugation is the opportunity for bacteria or other infectious agents to contaminate the cells. Even if all the materials are kept sterile, the repeated opening of the centrifuge tubes, and the exposure of pipettes and bottles of wash solution to the air can result in contamination. The risk of contamination is significant enough for some medical regulatory agencies to demand that only "closed" systems are used for cell handling.

Filtration methods have also been used to remove leukocytes from blood while retaining other blood constituents for later use. Such methods generally trap leukocytes on a filter in a non-recoverable form, while allowing other blood constituents to pass through the filter and into a collection vessel. For example, filters are available to remove leukocytes from blood so that the incidence of alloimmune reactions is minimized following blood transfusions. This removal is typically done using filters which are made of matted plastic fiber mesh. The mesh is usually arranged to trap the leukocytes in a reticulated matrix having enough depth so that the cells are trapped throughout the depth of the filter, thereby keeping the filter from clogging, as would occur if the leukocytes were trapped on a planar surface.

In addition to the physical trapping of the cells, the materials and large surface area of the filter allow leukocytes to adhere irreversibly to the surface. Many of these adherent cells are the very ones desired for some medical procedures. The resulting combination of trapping and adherence to the filter creates a highly efficient means of removing the leukocytes for disposal prior to blood infusion therapy. However, when leukocytes are the desired cells, this method of filtration is not advantageous.

A method that has been useful in the fractionation of various particles is tangential flow filtration (TFF) or "cross-flow" filtration. TFF relies on the movement of a fluid parallel to the surface of a porous membrane filter. The pores of the membrane allow passage of the fluid and of particles within the fluid that are smaller than the pores. In addition, the cross-flow (or "tangential" flow) of fluid parallel to the filter prevents a build-up of particles larger than the pores on the filter surface.

TFF has been used for the gross separation of various materials. The use of tangential flow filtration in the pharmaceutical field has been reviewed by Genovesi (*J. Parenter. Aci. Technol.*, 37:81, 1983), including the filtration of sterile water for injection, clarification of a solvent system, and filtration of enzymes from broths and bacterial cultures. Marinaccio et al. (WO 85/03011) report a process for use in the removal of particulate blood components from blood for plasmapheresis, and Robinson et al. (U.S. Pat. No. 5,423,738) describe the use of TFF for the removal of plasma from blood, allowing the reinfusion of blood cells and platelets into patients.

In another use, TFF has been reported for the filtration of beer (EP 0 208 450), specifically for the removal of particulates such as yeast cells and other suspended solids. Kothe et al. (U.S. Pat. No. 4,644,056) disclose the use of TFF in the purification of immunoglobulins from milk or colostrum, and Castino (U.S. Pat. No. 4,420,398) describes its use in the separation of antiviral substances, such as interferons, from broths containing these substances as well as viral particles and cells. Similarly, TFF has been used in the separation of bacterial enzymes from cell debris. (Quirk et al., *Enzyme Microb. Technol.*, 6:201, 1984.) In addition, tangential flow filtration units have been employed in the concentration of cells suspended in culture media. (See, e.g., Radlett, *J. Appl. Chem. Biotechnol.*, 22:495, 1972.)

TFF has also recently been reported to separate liposomes and lipid particles according to size. (Lenk et al., U.S. Pat. No. 5,948,441.) TFF allows for the formation and isolation of liposomes and lipid particles having a defined size range from heterogeneous populations of such particles. (See Lenk et al., supra).

However, while TFF has been used for gross fractionation of biological liquids and the separation of, for example, liposomes, the use of TFF for separation of different live cell populations having defined characteristics has not been appreciated in the art. In particular, the unique problems associated with the selective separation of leukocyte populations (such as, e.g., monocytes, CD34$^+$ hematopoietic stem and precursor cells, dendritic precursor cells, and the like) from other blood cells while maintaining sterility, cell viability, potential hematopoietic to differentiate, and immunotherapeutic cellular activity has not been addressed. In addition, the removal of other cell populations such as, e.g., populations with overlapping size ranges, has not been solved by current approaches.

Therefore, there remains a need in the art for additional devices and methods for selectively enriching leukocytes from other blood constituents, including plasma, erythrocytes, and/or platelets, while preserving sterility, cell viability, potential to differentiate, and immunotherapeutic cellular activity. The present invention satisfies these and other needs.

BRIEF SUMMARY OF THE INVENTION

The present invention relates to the separation of leukocytes from blood and blood preparations. In particular, a cell population enriched in leukocytes is prepared by the use of a tangential flow filtration device. Methods for the use of the device for the preparation of enriched leukocyte populations and cell populations enriched in monocytes, CD34$^+$ hematopoietic stem are precursor cells and the like are provided. The cell populations enriched in leukocytes and/or monocytes and the like obtained by the use of the devices and methods of the present invention can be used to prepare compositions of antigen presenting cells, e.g., antigen presenting dendritic cells, for administration to an individual for the induction of an immune response, prepare compositions of pluripotent stem cells, e.g., f-macrophage (f-MΦ), for induction to form epithelial, neuronal, endothelial, or hepatocyte cells, prepare compositions comprising enriched numbers of hematopoietic stem or precursor cells, and the like.

A tangential flow filtration device of the present invention comprises a remover unit having a cross-flow chamber, a filtrate chamber and a filter disposed therebetween. The filter is in fluid communication on one side, the retentate surface, with the cross-flow chamber, and on the other side, the filtrate surface, with the filtrate chamber. The cross-flow chamber has an inlet adapted to introduce a sample of blood constituents comprising leukocytes into the cross-flow chamber and parallel to the retentate surface of the filter. An outlet is also provided in the cross-flow chamber centrally disposed in a portion of the chamber opposite the retentate surface of the filter. The filter suitable for use in the tangential flow filtration device typically has an average pore size ranging from about 1 to about 10 microns. In certain embodiments the filter has an average pore size of about 3 to about 7 microns, or about 3 to about 5.5 microns.

Further, the device can comprise a means for providing a predetermined input rate of the sample into the inlet of the cross-flow chamber and a means for controlling a filtration rate of filtrate through the filter and into the filtrate chamber. The filtration rate controlling means limits the rate of filtration to less than the unopposed filtration rate for the filter. The sample comprising blood constituents can be provided by a source device such as a leukopheresis device or a container comprising a sample collected from, for example, a leukopheresis device, and the like.

The tangential flow filtration device can further comprise a recovery unit. The recovery unit comprising an inlet and an outlet can be interconnected in a loop format with the cross-flow chamber of the remover unit. In this embodiment of the device, the cross-flow chamber inlet is in fluid communication with the recovery unit outlet, and the cross-flow chamber outlet is in fluid communication with the recovery unit inlet. The recovery unit can further comprise a sample inlet and a wash inlet. In certain embodiments of the tangential flow filtration device the sample inlet and wash inlet are a single shared inlet. Typically, the wash inlet is in fluid communication with a source of replacement or wash fluid. The replacement or wash fluid can be, for example, an isotonic buffer or tissue culture media.

The sample inlet of the recovery unit is in fluid communication with a source of blood constituents. In one embodiment of the present invention the source of blood constituents is a cell-processing device. The cell processing device can be a leukopheresis device or a device that is capable of producing a cell population partially enriched for leukocytes. In one example, the cell processing device comprises a vessel having a first port and a second port, a monocyte dendritic cell precursor adhering substrate in fluid communication with the first port and the second port, a screen for retaining the substrate in the vessel and with a pore size sufficient to allow the passage of monocytic dendritic cell precursors and dendritic cells. The device further comprises a drain line in fluid communication with the first or second port and a collection line in fluid communication with the first and or second port which is also in fluid communication with the sample inlet of the recovery unit of the tangential flow filtration device.

The cell processing device can also comprise a plurality of fluid sources for providing binding media, washing buffer and elution buffer. The device can further comprise a pump for transferring the various fluids into and out of the cell processing device. A temperature controlling means, such as a heater or cooling device, can also be provided. In one embodiment of the present invention providing a closed system, a blood sample or blood product preparation is provided to the cell processing device comprising a bead material capable of adhering monocytic dendritic cell precursors. The blood sample is allowed to contact the bead material for a sufficient time to adhere the monocytic dendritic cell precursors and the device is washed of the other cell components through the drain line. The elution buffer is added to the cell processing device and the monocytic dendritic cell precursors are aseptically passed through the collection line into the sample inlet of the recovery unit for further enrichment of the blood sample of monocytes.

In one embodiment of the present invention, a tangential flow filtration device for enriching a sample of blood constituents for leukocytes is provided comprising a remover unit comprising a cross-flow chamber and a filtrate chamber separated by a filter, wherein the cross-flow chamber has an inlet and an outlet, the outlet centrally disposed in an upper portion of the chamber, and wherein the inlet is disposed above the filter and introduces fluid into the cross-flow chamber substantially parallel to the filter; a means for providing a predetermined input rate of the sample through the cross-flow chamber inlet; and a means for reducing a filtration rate through the filter; wherein the filter has a pore size of about 3 microns to about 7 microns; and whereby the sample is enriched for leukocytes in a retentate in the cross-flow chamber. Further, in another particular embodiment, the filter has a pore size of about 3 to about 5.5 microns to enrich the cell population for CD34$^+$ leukocytes.

In another embodiment of the present invention, a tangential flow filtration device for enriching a sample of blood constituents for monocytes is provided comprising a remover unit comprising a cross-flow chamber below a filtrate chamber and separated by a filter, wherein the cross-flow chamber has an inlet and an outlet, the outlet centrally disposed in a lower portion of the chamber, and wherein the inlet is disposed below the filter and introduces fluid into the cross-flow chamber substantially parallel to the filter; a means for providing a predetermined input rate of the sample through the cross-flow chamber inlet; and a means for maintaining a filtration rate through the filter; wherein the filter has a pore size of about 3 microns to about 7 microns; and whereby the sample is enriched for leukocytes in a retentate in the cross-flow chamber. Further, in another particular embodiment, the filter has a pore size of about 3 to about 5.5 microns to enrich the cell population for CD34$^+$ leukocytes.

In yet another embodiment of the present invention, a tangential flow filtration device for enriching a sample comprising blood constituents is provided comprising a remover unit (1) having a cross-flow chamber (3) and a filtrate chamber (4) separated by a filter (5), the cross-flow chamber having an inlet (6) and an outlet (7), the outlet disposed above the inlet and centrally disposed in an upper portion of the chamber, and wherein the filter is disposed below and substantially parallel to the cross-flow chamber inlet. The device further comprises a means for providing a predetermined input rate of the sample through the cross-flow chamber inlet; a means for providing a predetermined filtration rate of the fluid through the filter, wherein the predetermined filtration rate is about one-fifth to about one one-hundredth of the predetermined input rate; and a means for providing a predetermined concentration of blood cells in the sample, wherein the predetermined concentration of blood cells is typically about $10^7$ to about $10^{10}$ cells per milliliter. Typically, the filter has a pore size of about 3 microns to about 7 microns. Further, in another particular embodiment, the filter has a pore size of about 3 to about 5.5 microns to enrich the cell population for $CD34^+$ leukocytes.

The present invention also provides methods for separating leukocytes from a sample of blood constituents comprising leukocytes. In the methods step are provided comprising: (1) introducing the sample into a remover unit through an inlet in the remover unit; (2) subjecting the sample to cross-flow substantially parallel to a filter having a pore size of about 1 to about 10 microns; (3) subjecting the fluid to filtration through the filter; and (4) selectively removing non-leukocyte blood constituents from the sample to form a cell population enriched for leukocytes. The sample can be subjected to a partial purification or enrichment by leukopheresis, density centrifugation, differential lysis, filtration, or preparation of a buffy coat, for introduction in the remover unit. In one embodiment, the sample is induced to flow with a vortex motion in the cross-flow chamber. Additionally, the cell population enriched for leukocytes can be washed with a wash solution.

In the methods of the present invention the non-leukocyte blood constituents removed from the sample include plasma and platelets, erythrocytes, and the like. The leukocytes of the product from the methods of the invention can comprise a substantially enriched population of monocytes. The enriched cell population can comprise at least about 20% leukocytes, but typically comprises at least about 60% or more leukocytes. In one embodiment of the method of the present invention steps (1), (2), and (3) are repeated at least two times to form cell population enriched for leukocytes. The cell population enriched for leukocytes can further be used for the preparation of monocytic dendritic cell precursors. In one embodiment the enriched cell population is produced by a method comprising contacting a monocytic dendritic cell precursor adhering substrate with the cell population enriched for leukocytes; allowing monocytic dendritic cell precursors in the cell population to reversibly adhere to the substrate to form complexes comprising monocytic dendritic cell precursors and substrate; separating the complexes from the non-adhering leukocytes to obtain complexes comprising monocytic dendritic cell precursors; and culturing the monocytic dendritic cell precursors to differentiate the precursors to form immature or mature dendritic cells. In one particular embodiment the monocytic dendritic cell precursors are eluted from the substrate prior to culturing. The substrate for adhering the monocytic dendritic cell precursors can comprise glass, polystyrene, plastic, or glass-coated polystyrene microbeads.

In still another embodiment of the present invention a method for enriching a sample of blood constituents for leukocytes is provided comprising: (1) introducing the sample into a tangential flow filtration (TFF) unit, the TFF unit comprising a cross-flow chamber, a filtrate chamber, and a filter in fluid communication with the cross-flow chamber and the filtrate chamber, the filter having a pore size of about 1 to about 10 microns; (2) recirculating the sample through the TFF unit at a predetermined input rate and a predetermined filtration rate, the predetermined input rate at least five times the predetermined filtration rate; wherein the predetermined filtration rate is less than the unopposed filtration rate for the filter; and (3) isolating a cell population enriched for leukocytes. The method can result in an enriched cell population that is substantially free of non-leukocyte blood constituents including plasma, platelets and erythrocytes. The enriched cell population produced by this method can comprise at least about 20% leukocytes, and typically at least about 60% or more leukocytes. The method can further comprise the collecting of blood from a subject and preparing the sample from the blood by leukopheresis, density centrifugation, differential lysis, filtration, or preparation of a buffy coat.

Once the cell population has been enriched for leukocytes the method can further comprise preparing a particular cell type that can be induced from the leukocytes, such as, for example, dendritic cell precursors, $CD34^+$ hematopoietic stem cells, or pluripotent stem cells, such as, f-macrophage, and the like. In one particular embodiment dendritic cells can be prepared from the enriched cell population. In this method the dendritic cells are prepared by: contacting a monocytic dendritic cell precursor adhering substrate with the enriched cell population; allowing monocytic dendritic cell precursors in the enriched cell population to reversibly adhere to the substrate to form complexes comprising monocytic dendritic cell precursors and substrate; separating the complexes from the non-adhering leukocytes to obtain complexes comprising monocytic dendritic cell precursors; and culturing the monocytic dendritic cell precursors to differentiate the precursors to form immature or mature dendritic cells. The substrate can comprise glass, polystyrene, plastic or glass-coated polystyrene microbeads. Additionally, the monocytic dendritic cell precursors can be cultured with cytokines that promote the differentiation of monocytes into dendritic cells. In a particular embodiment the cytokines are GM-CSF and IL-4. Further, the dendritic cells can be matured to mature dendritic cells.

Once the dendritic cell precursors have been isolated, the dendritic cells can be cultured with an antigen under conditions conducive for processing the antigen to form antigen loaded dendritic cells. The antigen loaded dendritic cells can then be administered to an individual or the antigen loaded dendritic cells can be cultured in vitro or ex vivo with T cells to induce the formation of antigen specific cytotoxic T cells. The cytotoxic T cells can be administered to an individual in need of an induced antigen specific immune response, such as in the treatment of cancer and bacterial or viral infection.

A cell population enriched for hematopoietic stem cells can be produced. In one embodiment, an individual can be provided with a stem cell mobilizing agent, such as for example, G-CSF, GM-CSF, AMD3100 (or other agents that inhibit CXCR-4 function), or high- or low-dose cyclophosphamide, and the like. The stem cell mobilizing agent induces the proliferation of $CD34^+$ stem cells which are released into the peripheral blood steam. A leukapheresis sample from the individual is introduced into a tangential flow filtration (TFF) unit, the TFF unit comprising a cross-flow chamber, a filtrate chamber, and a filter in fluid communication with the cross-flow chamber and the filtrate chamber, the filter having a pore size of about 3 to about 5.5 microns; (2) recirculating the sample through the TFF unit at a predetermined input rate and a predetermined filtration rate, the predetermined input rate at least five times the predetermined filtration rate; wherein the predetermined filtration rate is less than the unopposed filtration rate for the filter; and (3) isolating a cell population enriched for CD34+ leukocytes. The method can result in an enriched cell population that is substantially free of non-leukocyte blood constituents including plasma, platelets and erythrocytes. The enriched cell population produced by this method can increase the percentage of CD34+ cells 2 to 5 fold from 1% to about 5% of leukaphoresis material to about 10% to about 40% of the cells in an enriched cell population.

Further, monocytes isolated as described above can be cultured in M-CSF containing medium in a non-adhesive cell culture container, e.g., a Teflon culture bag. Culture of the monocytes in M-CSF results in the production of a substantial number of CD34+ cells. Cell populations enriched in leukocytes or monocytes as described above can also be cultured in the presence of a number of other cytokines and leukokines known in the art to induce the production of a number of other progenitor cell types. for example, the cell population enriched in leukocytes and/or monocytes can be cultured in the presence of VEGF, bFGF, IGF-1, EGF and fetal serum on a fibronectin coated surface and discarding non-adherent cells to obtained endothelial-like circulating angiogenic cells, or f-MΦ can be differentiated into epithelial cells by culturing in EGF, differentiated into neuronal and endotherlial cells by incubation in NGF or VEGF respectively or differentiated into hepatocytes by incubating in the presence of HGF, and the like.

BRIEF DESCRIPTION OF THE DRAWINGS

FIG. 1A provides an embodiment of the device for the enrichment of leukocytes wherein the cross-flow chamber is above the filtration chamber. FIG. 1B depicts a front view of the device wherein the input of sample is below the filter and the filtrate passing upward through the filter for the enrichment of monocytes. FIG. 1C is an overhead view of the device depicted in FIG. 1B.

DESCRIPTION OF THE SPECIFIC EMBODIMENTS

Figure 1A:
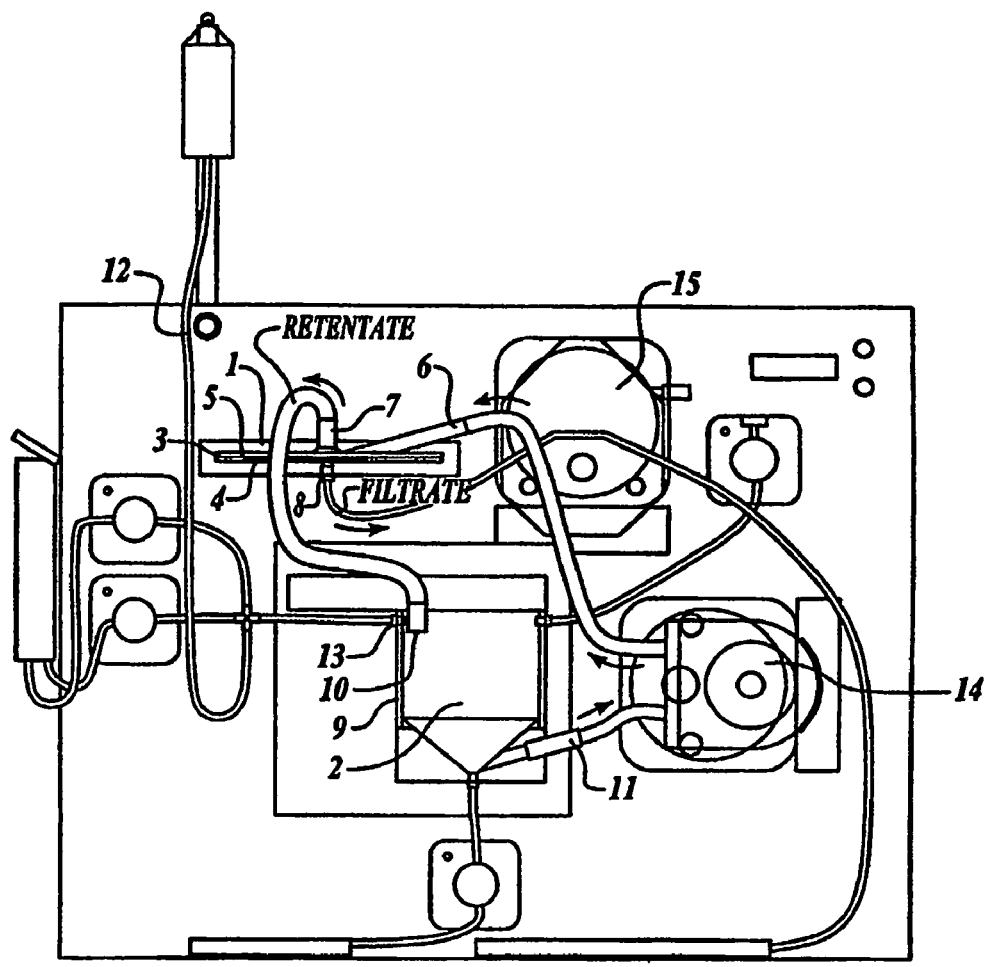
FIGS. 1A through 1C depict embodiments of the tangential flow filtration device for the separation of leukocytes and also monocytes from a blood product-sample.

The present invention provides devices and methods for processing a heterogenous mixture of blood constituents to provide an enriched population of leukocytes. In one aspect of the invention, devices and methods are provided for the enrichment of leukocytes by the selective removal of non-leukocyte blood constituents, e.g., plasma, platelets and/or erythrocytes, and the like. In another aspect, devices and methods are provided for the enrichment of monocytes by the selective removal of non-monocyte blood constituents, including, for example, the removal of lymphocytes, erythrocytes, platelets and the like from the mixture.

An enriched population of leukocytes is typically prepared from a sample, or fluid mixture, comprising blood constituents. The term "blood constituents" as used herein refers to any material typically present in blood, including such material typically present in diseased as well as non-diseased states. Blood constituents include leukocytes and can include, for example, lymphocytes, monocytes, erythrocytes, neutrophils, eosinophils, natural-killer (NK) cells, and/or platelets, soluble or insoluble protein or protein complexes (e.g., enzymes, immunoglobulins, or immunoglobulin-antigen complexes), other macromolecular components such as, e.g., lipids, or any other portion of whole blood that can be physically separated, irrespective of its precise molecular or cellular makeup, including, e.g., plasma or serum.

The sample, or fluid mixture, can be partially enriched for leukocytes prior to carrying out the methods of the present invention. The term "leukocyte" is used interchangeably with the term "white blood cells" ("WBCs"). These terms include mononuclear agranulocytes, which include, e.g., monocytes, dendritic cell precursors, and lymphocytes, as well as polymorphonuclear granulocytes with segmented nuclei and cytoplasmic granules, including neutrophils, eosinophils, basophils, and mast cells. "Monocyte" refers to a class of myeloid-derived leukocytes, generally larger than lymphocytes, with an ovoid or kidney-shaped nucleus, typically containing lysosomal granules and typically expressing CD14.

In certain aspects of the present invention, lymphocytes are separated from the leukocytes. "Lymphocyte" refers to cells derived from lymphoid progenitor cells and includes B-lymphocytes, T-lymphocytes, and natural-killer (NK) cells. The term "small lymphocytes" refers to lymphocytes that are about 7-8 microns in diameter.

As used herein, the term "population of leukocytes" refers to any group of cells that includes leukocytes. A population of leukocytes can include a broad range of leukocyte sub-types or of particular sub-types, such as, e.g., monocytes and/or monocytic dendritic precursor cells. The terms "enrichment", "enrich" and "enriched" mean that the processing of a mixture of blood constituents using the devices, or following the methods of the present invention results in a cell population having a higher percentage of viable leukocytes, in relation to other constituents, than the initial mixture (i.e., prior to enrichment). As used herein, the term "viable" refers to a leukocyte that is capable of differentiation under suitable culture conditions.

The devices according to the present invention utilize tangential flow filtration to enrich for a population of leukocytes. The terms "tangential flow filtration" and "cross-flow filtration" are used interchangeably and refer to the separation of suspended particles (e.g., cells) from a fluid mixture, including the separation of particles of a defined characteristic (e.g., a desired size range) from a heterogeneous mixture of particles in the fluid mixture. The particles are separated by passing or circulating the fluid mixture (e.g., a sample fluid) in a sample chamber substantially parallel or tangential to a filter (e.g. the surface of the filter facing the sample fluid), typically under some positive pressure, with the fluid mixture comprising the concentrated particles, or leukocytes, continuing to flow tangential to the membrane surface.

Generally, determination of which particles are removed in the "filtrate," i.e., that portion of fluid passing through the filter, and those particles retained in the "retentate" is dependent on a variety of factors. Such factors include, e.g., filter pore size, input rate, filtration rate, concentration of particles in the fluid mixture, temperature, and viscosity of the fluid mixture. As used herein, "pore size" refers to the average size of the pores in the filter. "Input rate" refers to the rate at which a sample (e.g., fluid mixture) is introduced into the chamber housing the filter. Where the sample is recirculated multiple times across a filter (e.g., in a device according to the present invention), the input rate is also referred to as the "recirculation rate." "Cross-flow" refers to the substantially parallel (i.e., parallel to the surface of the filter in any direction) flow of the fluid mixture across the filter. "Cross-flow rate" refers to the rate of flow of sample, or fluid mixture, over and substantially parallel to the filter; the cross-flow rate of the fluid mixture is generally dependent on a variety of parameters, including, for example, the input rate and the size and shape of the chamber housing the filter. "Filtration rate" refers to the rate of flow of the fluid mixture through the filter. The filtration rate for a device and the methods according to the present invention is typically less than the unopposed (i.e., open tube) filtration rate. "Output rate" refers to the rate of removal of the fluid mixture from the cross-flow chamber, other than the fluid mixture passing through the filter (i.e., the filtrate). The output rate is generally equal to the input rate minus the filtration rate.

As used herein, the term "filter" refers to any article made of any material or combination of materials having a plurality of pores that allow one or more components (e.g., blood constituents) of a sample or fluid mixture subjected to cross-flow across the article to pass through it, thereby separating those components (e.g., non-leukocytes) from other components (e.g., leukocytes). The surface of a filter can have any suitable area, such as, for example, about 42 to about 145 mm in diameter, although filters of greater and lesser area can be used. In certain embodiments, only one filter is used in a TFF device. In other embodiments, additional filters can be used in a TFF device.

The filter typically employed in the TFF device of the present invention can be chosen from a wide range of organic polymeric filters. Such filters include, but are not limited to, microporous membranes of nylon, polyvinylidene fluoride (PVDF), cellulose acetate/nitrate, polysulfone, polycarbonate, polyethylene, polyester, polypropylene, and polyamide. Other filters, such as ceramic filters and metallic filters, can also be used. Both hydrophilic and hydrophobic, charged and uncharged filters can be used. In certain applications, hydrophilic filters can be preferred.

A filter of the present invention typically comprises a number of pores distributed across the area of the filter. In certain embodiments, the filter has a pore size with a small variation in pore size. For example, the variability in the pore size can be about ±20%, or within the range of about +0 to about 20%. In a typical embodiment, "nuclepore" or "track etched" filters are used (e.g., Poretics® polyethylene or polycarbonate track-etched filter membranes (Osmonics, Minnetonka, Minn.)). These filters typically have a smooth surface with tightly controlled pore sizes in the material. Such filters are typically prepared by exposing a flat sheet of non-porous plastic to a source of radioactive particles, which are energetic enough to pierce to plastic sheet. The "tracks" are then enlarged in diameter by exposure to chemical solvents or etching agents. The size of the pores can be controlled by the track etching conditions.

The present invention takes advantage of differences between various cell types in blood to enrich for leukocytes (e.g., monocytes, dendritic cell precursors, and the like). Such differences can include, e.g., differences in size, shape and/or deformability. The size and deformability of cells in human blood typically varies by cell type. Erythrocytes (red blood cells) are typically biconcave disk shaped, enucleate, measure about 7 microns in the major diameter and are relatively deformable. Polymorphonuclear leukocytes cells are typically spheroidal, also about 7 microns, but less deformable than erythrocytes. Of the mononuclear cells, lymphocytes are typically 7 to 10 microns, and monocytes usually are in the range of 10 to 15 microns.

In various embodiments, the filter pore size is selected to enrich for leukocytes, and/or to fractionate blood constituents, thereby enriching for leukocytes. For example, in certain embodiments, monocytes having a nominal diameter of 10 to 15 microns, and erythrocytes having a nominal diameter of 7 microns, can be separated by TFF using a filter having a pore size of about 5 to about 5.5 microns. In a particular embodiment a filter of 4.5 microns was used to successfully separate monocytes from the other cellular constituents of a leukopheresis sample.

In other embodiments, the filter pore size can be within the range of about 1 to about 10 microns, or about 3 to about 8 microns, or about 3 to about 5 microns. A filter pore size in the range of about 3 microns can retain most leukocytes, and effect less efficient removal of erythrocytes from the leukocytes. In contrast, a filter pore size in the range of about 8 microns can effect more efficient removal of erythrocytes, but increases the loss of leukocytes in the filtrate. A filter size of about 3 to about 5.5 microns can be used to enrich for $CD34^+$ hematopoietic stem cells.

The enrichment of leukocytes from other cellular blood constituents can also be affected by the input rate, the filtration rate, and/or the concentration of cells in the sample or fluid mixture. For example, erythrocytes are more deformable than leukocytes and can, therefore, be more readily passed through a filter pore size smaller than the major diameter of the erythrocytes (e.g., less than about 7 microns). In a specific example, erythrocytes can be separated from leukocytes using filters having pore size of about 5 microns. In other embodiments, the filter pore size is decreased to about 3 microns, and the concentration of cells increased (supra) to efficiently separate erythrocytes from leukocytes.

The enrichment of leukocytes from other cellular blood constituents can also be affected by maintaining a filtration rate that is less than the unopposed (i.e., open tube) filtration rate under the same input or recirculation rate. In other embodiments, the loss of leukocytes to the filtrate can be reduced by maintaining an input or recirculation rate that is greater than the filtration rate. In exemplary embodiments, the input or recirculation rate can be at least about five time, at least about 10 times, at least about 20 times, at least about 50 times, or at least about 100 times, the filtration rate.

A sample, or fluid mixture, comprising various blood constituents for cell fractionation by TFF can be obtained from a variety of sources and can include fluid mixtures of blood products at any of the various stages of processing. For example, blood sources can be either human or non-human. In addition, fluid mixtures can be, for example, whole blood, various dilutions of whole blood, or whole blood or blood dilution that has been subjected to processing by, e.g., removal of plasma or other blood constituents. Thus, the fluid mixture can include, for example, a blood cell population that is already at least partially enriched for leukocytes.

Blood constituents, or populations of leukocytes, can be prepared by methods known to those skilled in the art. Such methods typically include collecting heparinized blood, apheresis or leukopheresis, preparation of buffy coats, resetting, centrifugation, density gradient centrifugation (e.g., FICOLL-HYPAQUE®, PERCOLL®, sucrose, and the like), differential lysis of non-leukocyte cells, filtration, and the like. A leukocyte population can also be prepared by collecting blood from a subject, defibrinating to remove the platelets and lysing the majority of red blood cells. The population of leukocytes can optionally be enriched for monocytes by, for example, centrifugation through a PERCOLL® gradient.

The fluid mixture comprising the blood constituents can optionally be diluted or concentrated, as desired. For example, in certain embodiments, the blood constituents are diluted 1:2, 1:5, 1:10, or any other suitable dilution. Blood constituents can be diluted in, for example, isotonic buffers (e.g., PBS or HEPES-buffered saline), tissue culture media and the like. Typically, the sample of blood constituents subjected to TFF has a cell concentration of about $10^6$ to about $10^8$ cells per ml.

Blood cell populations can be obtained from a variety of types of subjects, according to the desired use of the enriched population of leukocytes. The subject can be a healthy subject. Alternatively, blood cells can be obtained from a subject in need of immunostimulation, such as, for example, a cancer patient or other patient for which immunostimulation may be beneficial. Likewise, blood cells can be obtained from a subject in need of immune suppression, such as, for example, a patient having an autoimmune disorder (e.g., rheumatoid arthritis, diabetes, lupus, multiple sclerosis, and the like). A blood cell population also can be obtained from an HLA-matched healthy individual for administration to an HLA-matched patient in need of immunostimulation. A blood cell population can also be collected from an individual that has been administered a stem cell mobilization agent such as for example GM-CSF, G-CSF, AMD3100 (or other agent that inhibits CXCR-4 function), or low- or high-dose cyclophosphamide (Deliliers et al., *Leuk. Lymphoma* 43:1957, 2002) and the like. The individual can be a patient that wilt received enriched cell population, a relative, or a HLA-matched individual.

In certain embodiments, the enriched population of leukocytes can be collected in the retentate, while other blood constituents pass into the filtrate. For example, for enrichment of a population of leukocytes (e.g., including monocytes and lymphocytes), other blood constituents such as plasma, platelets, and/or erythrocytes can be among the constituents selectively removed into the filtrate. In additional embodiments, lymphocytes, or small lymphocytes, can be selectively removed and passed into the filtrate.

Figure 1B:
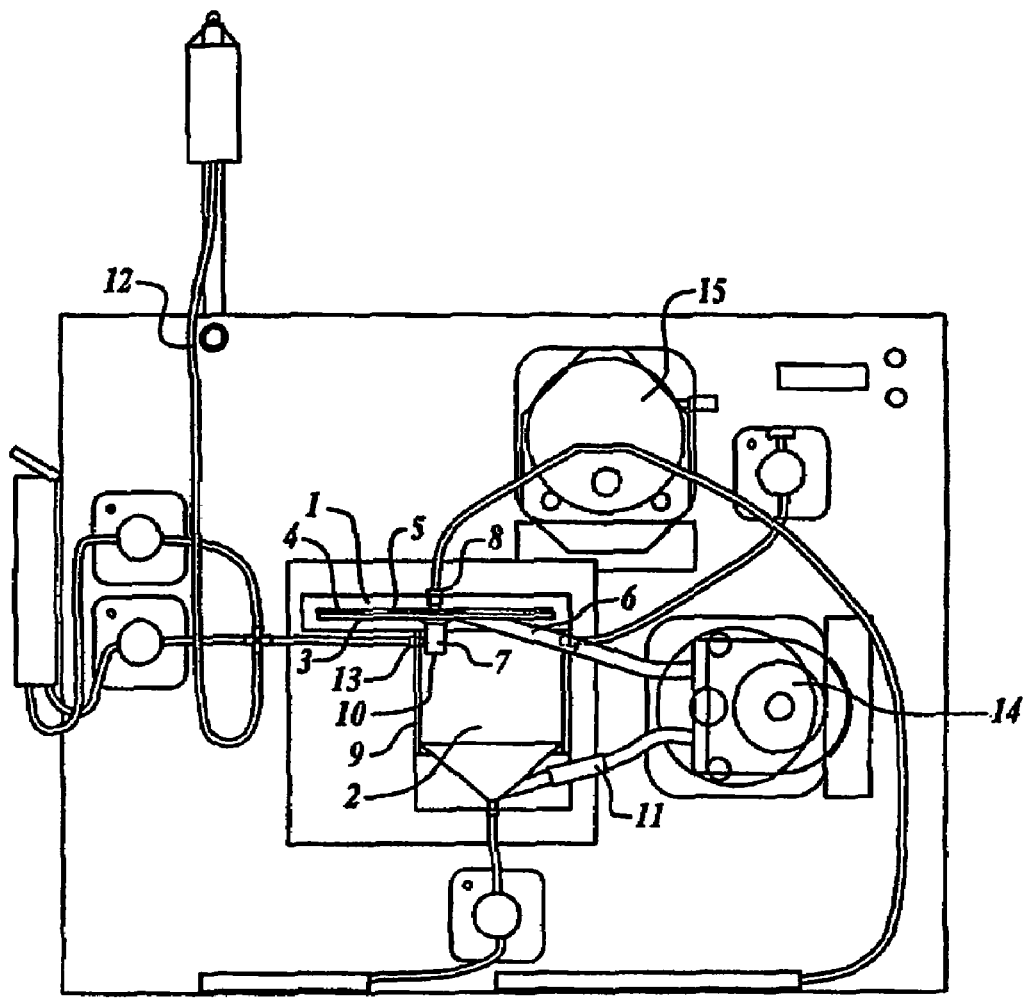
Figure 1C:
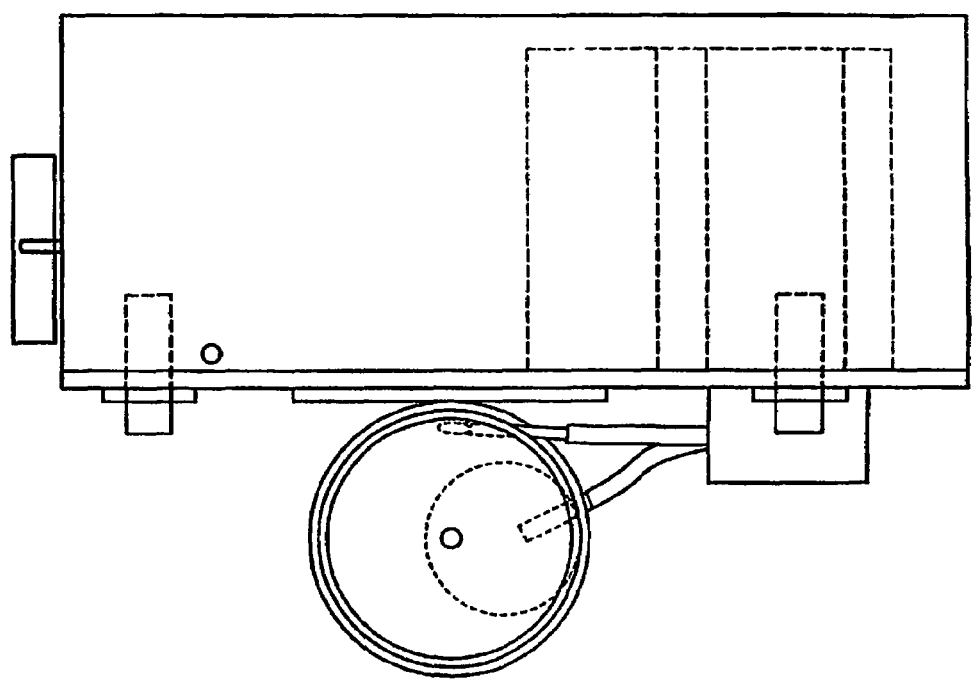

The devices according to the present invention as depicted in FIGS. 1A through 1C typically comprise a cross-flow chamber (3) and a filtrate chamber (4). A filter (5) is positioned between and with one surface in fluid communication with the cross-flow chamber (the retentate surface) and other surface in fluid communication with the filtrate chamber (the filtrate surface). The cross-flow chamber, filtrate chamber and filter comprise a remover unit (1). In one embodiment, the cross-flow chamber typically has a volume of about 55 ml, and the filtrate chamber has a volume of about 25 ml. The filter diameter is typically substantially the same as the diameter of the cross-flow chamber. In certain embodiments used to demonstrate the utility of the present invention, the filter is about 140 mm to about 143 mm in diameter.

The fluid mixture enters the cross-flow chamber (3) through a fluid inlet (6) that is typically situated adjacent to the retentate surface of the filter and such that the fluid mixture (e.g., sample) enters the chamber substantially parallel to the retentate surface of the filter. Typically, fluid is removed from the cross-flow chamber (3) through a fluid outlet (7), which is usually located at a portion of a cross-flow chamber perpendicular to the retentate surface of the filter. In certain exemplary embodiments, the cross-flow chamber inlet (6) diameter is about 7 mm to about 8 mm, and cross-flow chamber outlet (7) diameter is about 8 mm to about 10 mm. The filtrate is removed through an outlet (8) in the filtrate chamber (4).

Typically, the fluid mixture is introduced into the cross-flow chamber at a sufficient input rate such that the cross-flow of the fluid mixture across the surface of the filter (retentate surface) is at a velocity high enough to gently disrupt and back-mix fluid and cells at the contact surface of the filter, i.e., the boundary layer. As used herein, "boundary layer" refers to that layer of fluid adjacent to and on the retentate side of the filter, typically left by fluid passing through the filter. This disruption of the boundary layer facilitates efficient filtration by preventing the material at the contact surface of the filter from binding to the filter or becoming stagnant, which can hinder efficient filtration. The input rate of the fluid mixture is usually not sufficient, however, to cause lysis of a substantial number of leukocytes.

In certain embodiments, the blood constituents are passed across the retentate surface of the filter by pumping the fluid mixture into the cross-flow chamber (3). The pump used to drive the cross-flow of fluid across the filter is referred to as the "cross-flow pump" or "recirculating pump" (14). The cross-flow pump can include any pumping device in fluid communication with the cross-flow chamber (3) sufficient to introduce the flow of fluid into the chamber and across the filter at the specified input rate, without causing substantial damage to the cells (e.g., cell lysis). A cross-flow pump suitable for use in the present invention can include, e.g., a peristaltic pump, piston pump, diaphragm pump, or roller pump. A peristaltic pump can be used, for example, where it is desired to maintain the TFF device as part of a "closed" system.

The fluid mixture is typically pumped into the cross-flow chamber (3) at an input rate that exceeds the filtration rate. In an exemplary embodiment, the input rate is about 1680 ml/minute, and the filtration rate is about 15 ml/minute. In other exemplary embodiments, the input rate is about 1600 to about 1800 ml/minute, and the filtration rate is about 10 to about 20 ml/minute. Non-leukocytic material (e.g., erythrocytes, immune complexes, proteins, and the like) pass through the filter (5) into a filtrate chamber (4).

As discussed supra, the filtration rate is typically less than the unopposed (i.e., open tube) rate. The filtration rate can be controlled, for example, by reducing or restricting the size of the filtrate chamber outlet, by use of a second pump means (e.g., a "filtration pump") to restrict the flow, and the like.

In another exemplary embodiment, the introduction of a fluid mixture into the device creates a vortex motion within the fluid. This can be done, for example, by introducing the fluid mixture, for example substantially parallel to a circular filter in a cylindrical cross-flow chamber, at an input rate about 5 or about 10 to about 100 times the filtration rate. The flow through is removed by means of an outlet (7) located in the cylindrical chamber perpendicular to the filter and typically adjacent to the center of the filter surface. This arrangement causes the flow to spiral inward toward the center of the filter. The flow is typically not turbulent, or at such a high rate, so as to cause substantial lysis of the leukocytes. As discussed above, the flow can also "scrub" the filter surface to prevent binding or stagnation at the boundary layer. By calibrating the input rate such that it is large (e.g., at least about 5 times) relative to the filtration rate, the resulting enriched population of leukocytes can be at least about 20, or at least about 40 percent, or more, leukocytes.

In another exemplary embodiment, the retentate is recirculated to increase efficiency of separation. For example, a fluid mixture comprising blood constituents can be introduced into the cross-flow chamber, and then retentate can be withdrawn through the fluid outlet (7) in the cross-flow chamber to another chamber, such as, e.g. a chamber from which the fluid was initially provided ("a recovery unit"; (2)). The fluid mixture in the recovery unit can then be re-introduced into the cross-flow unit. By connecting the recovery unit (2) and remover unit (1) in "loop format," continuous recirculation and filtration of the fluid mixture can be achieved. Alternatively, the retentate can be withdrawn through the fluid outlet (7) of the cross-flow chamber (3) and directly reintroduced into the cross-chamber inlet (i.e., without passing through a recovery unit or another chamber). The fluid mixture can be passed through the cross-flow unit for any suitable period of time. In certain embodiments, the fluid mixture can be recirculated for about 5 to about 60 minutes, or more, to achieve the desired leukocyte cell purity or enrichment.

In yet another embodiment, the volume of the fluid mixture can be adjusted by adding a buffer, a wash solution or other solution (collectively referred to as a "replacement liquid"). The wash solution can, for example, be combined with a fluid mixture in a recovery unit (e.g., through a solution inlet; (13)), in a remover unit, at a pump (14), in tubing extending to or from the remover unit, or at any other convenient location. The cells in the retentate can thus be enriched and washed in the same operation. Typically, the wash solution is isotonic with the cells. Suitable buffer and wash solutions can include a variety of buffers (e.g., phosphate-buffered saline (PBS) or HEPES-buffered saline), tissue culture media, and the like.

In certain embodiments, cell populations are enriched for a population of leukocytes in a closed, aseptic system. As used herein, the terms "closed, aseptic system" or "closed system" refer to a system in which exposure to non-sterile, ambient, or circulating air or other non-sterile conditions is minimized or eliminated. Closed systems for enriching cell populations generally exclude centrifugation in open top tubes, open air transfer of cells, culture of cells in tissue culture plates or unsealed flasks, and the like. The entire filtration system, including, e.g., any cell containers, incubators, tissue culture vessels, or other apparatus for cell processing (infra), can be maintained as a "closed" system. In a typical embodiment, the closed system allows aseptic enrichment of leukocytes and, optionally, transfer from an initial collection vessel to a sealable tissue culture vessel, without exposure to non-sterile air. Typically, a peristaltic pump (FIGS. 1A and 1C; (15)) means is used in a closed system.

In another aspect of the invention, a heterogeneous mixture of blood constituents is substantially enriched for leukocytes by the selective removal from the mixture of non-leukocyte blood constituents, including, e.g., plasma, platelets, erythrocytes, and the like. As used herein, the term "substantially enriched" means that the cell population recovered in the retentate, following as many cycles of recirculation as desired, is comprised of at least about 20%, or at least about 40%, or at least about 60%, of the desired cell type (e.g., leukocytes). In other embodiments, a heterogeneous mixture of blood constituents is enriched for leukocytes to form an enriched population of leukocytes that is substantially free of non-leukocyte blood constituents. As used herein, the term "substantially free" means that the enriched population of leukocytes comprises at least 50% leukocytes.

In an exemplary embodiment of this aspect of the present invention, the TFF device comprises a cross-flow chamber (3) with a volume of about 55 ml and a filtrate chamber (4) with a volume of about 25 ml. Further the device comprised the following: a filter pore size of about 1 to about 10 microns, or about 2 to about 8 microns, or about 3 to about 5 microns; an input rate of about 1600 to about 1800 ml/min; a filtration rate of about 12 to about 17 ml/min, and a filter diameter of about 142 mm. The initial fluid mixture typically has a cell concentration of at least about $10^7$ cells per ml (e.g. leukocytes and other cells).

In another aspect of the invention, a heterogeneous mixture of blood constituents is substantially enriched for monocytes by the selective removal of non-monocyte blood constituents, including, for example, the removal of lymphocytes from the mixture. As used herein, the terms "selective removal", "selectively removed" and "selectively removing" refer to the preferential removal of one cell type and enriching for another cell type. In an exemplary embodiment of this aspect, the TFF device comprises a cross-flow chamber (3) with a volume of about 55 ml and a filtrate chamber (4) with a volume of about 25 ml. Further, the device comprised the following: a filter pore size of about 1 to about 10 microns, or about 2 to about 8 microns, or about 3 to about 5 microns; an input rate of about 1600 to about 1800 ml/min; a filtration rate of about 12 to about 17 ml/min; and a filter diameter of about 142 mm. The initial fluid mixture typically has a cell concentration of at least about $10^7$ cells per ml (e.g., monocytes and other cells). In this embodiment the device was operated in an inverted manner.

Culture, Expansion and Differentiation of Enriched Cell Populations

Following enrichment of a leukocyte cell population as described, supra, the leukocytes optionally can be cultured to maintain their viability, increase cell numbers and/or differentiate the cells to another cell type. Suitable tissue culture vessels, include, for example, tissue culture flasks, bags, plates, bioreactors (including a fermenter), and the like.

In an exemplary embodiment, the enriched population of leukocytes can be cultured in a closed, aseptic system, such as a bioreactor, tissue culture bag, and the like. The closed system can have an inlet and/or outlet for the controlled, aseptic introduction or removal of fluids (e.g., tissue culture media, washing buffer), gases, cells, and the like.

In another exemplary embodiment, an enriched population of leukocytes can be transferred to a bioreactor. The bioreactor can be equipped with appropriate inlets and/or outlets for introducing cells, sterile gas (e.g., oxygen, carbon dioxide, and/or air), tissue culture media, and the like. The bioreactor can also have means for controlling the temperature. The bioreactor is typically operated at about 37° C. The bioreactor also can include means for agitating the cells and/or culture medium in the bioreactor. The agitation means can include, for example, a paddle or a spin filter (which also can function as an outlet for media).

In yet another exemplary embodiment, an enriched population of leukocytes can be transferred to closed system, such as a tissue culture bag. Suitable tissue culture bags include, for example, STERICELL® culture containers (Nexell Therapeutics Inc.) or TEFLON® culture bags (American Fluoroseal Corp.). The closed system can have any suitable size or volume, as will be appreciated by the skilled artisan. Suitable volumes include, for example, from about 0.01 liters to about 5 liters, or about 0.01 liters to about 0.05 liters, although greater and lesser volumes are possible and within the scope of the present invention.

In various embodiments according to the present invention, cell populations enriched for leukocytes (e.g., including monocytes, monocytic dendritic cell precursors, $CD34^+$ hematopoietic stem cells, or other precursor cells) optionally can be cultured and differentiated by the addition of an appropriate inducing agent to obtain cells of a particular cell type, including for example, immature or mature dendritic cells, f-macrophage, $CD34^+$ hematopoietic stem or precursor cells or other precursor cells. Suitable tissue culture media include, for example, AIM-V, RPMI 1640, DMEM, X-VIVO 15™, and the like. The tissue culture medium can be supplemented, as desired, with amino acids, vitamins, cytolines, such as granulocyte/macrophage colony stimulating factor (GM-CSF) and/or interleukin 4 (IL-4), divalent cations, and the like, to promote differentiation of the cells to, immature dendritic cells, for example. A typical cytokine combination is about 500 units/ml each of GM-CSF and IL-4.

The enriched population of leukocytes can be cultured for any suitable time. In certain embodiments, suitable culture times for the differentiation of cells to immature dendritic cells can be about 4 to about 7 days. The differentiation of immature dendritic cells from precursors can be monitored by methods known to those skilled in the art, such as by the presence or absence of cell surface markers (e.g., $CD14^-$, $CD11c^+$, $CD83^{lo}$, $HLA-DR^+$). Immature dendritic cells can also be cultured in appropriate tissue culture medium to expand the cell population and/or maintain the immature dendritic cells in a state for further differentiation or antigen uptake, processing and presentation. For example, immature dendritic cells can be maintained in the presence of GM-CSF and IL-4.

In certain embodiments, immature dendritic cells are preferred for optimal antigen presentation because they retain the ability to process new antigen (See, e.g., Koch et al., *J. Immunol.* 155: 93-100, 1995.) In contrast, mature dendritic cells (e.g., $CD14^-$, $CD11c^+$, $CD83^+$, $CD86^+$, $HLA-DR^+$), those that have been exposed to and process antigen and to suitable maturation agents, have typically lost the ability to efficiently process new antigens.

During culture, immature dendritic cells can optionally be exposed to a predetermined antigen. Suitable predetermined antigens can include any antigen for presentation to T-cells (e.g., for activation, stimulation of proliferation, induction of anergy, and the like). In one embodiment, immature dendritic cells are cultured in the presence of a tumor associated antigen, such as, for example, prostate specific membrane antigen (PSMA) (e.g., for cancer immunotherapy and/or tumor growth inhibition). Other antigens can include, for example, bacterial and viral antigens, tumor specific or tumor associated antigens (e.g., tumor cell lysate, tumor cell membrane preparation, isolated antigens from tumors, fusion proteins, liposomes, and the like), and any other antigen. Following contacting with antigen, the cells can be cultured for any suitable time to allow antigen uptake and processing, to expand the population of antigen-specific dendritic cells, and the like. Immature dendritic cells can also be matured into mature dendritic cells that present antigen in the context of MHC molecules. Such maturation can be performed, for example, by culture in the presence of maturation factors, such as cytokines (e.g., TNF-α), bacterial products (e.g., BCG), and the like.

In yet another aspect of the invention, a heterogeneous mixture of blood constituents is substantially enriched for monocytic dendritic precursor cells. Following enrichment of a population of cells for leukocytes or monocytes, as described supra, monocytic dendritic cell precursors, such as those from peripheral blood, can be isolated from the enriched population through selective adherence to a substrate (e.g., a monocytic dendritic cell precursor binding substrate). Such a substrate can be provided by, for example, a tissue culture dish or flask. Alternatively, a substrate having a high surface area to volume ratio, such as a particulate or fibrous substrate, as disclosed in PCT/US02/23865, filed 25 Jul. 2002, the disclosure of which is incorporated by reference herein), can be used. The monocytic dendritic cell precursors can be monocytes that selectively adhere to the substrate to form complexes of monocytic dendritic cell precursors and substrate, while other leukocytes remain unbound ("non-adhering"). The bound leukocytes are then separated from the unbound leukocytes to form a population of cells enriched in monocytic dendritic cell precursors on the substrate. The monocytic dendritic cell precursors can be cultured and differentiated on the substrate, or eluted from the substrate and then cultured and differentiated separately, to obtain immature and/or mature, antigen-presenting dendritic cells. In accordance with this aspect, the monocytic dendritic cell precursors optionally can be isolated and differentiated in a closed, aseptic system.

According to another aspect, dendritic cells exposed to a predetermined antigen can be used to activate T cells in vitro or in vivo against the antigen. The dendritic cells optionally can be used immediately after exposure to antigen to stimulate T cells. Alternatively, dendritic cells can be maintained in the presence of a combination of cytokines (e.g., GM-CSF and IL-4) prior to exposure to antigen and T cells. In a specific embodiment, human dendritic cells are used to stimulate human T cells in vitro or in vivo.

T cells or a subset of T cells can be obtained from various lymphoid tissues. Such tissues include but are not limited to the spleen, lymph nodes, and peripheral blood. T cell purification can be achieved, for example, by positive or negative selection including, but not limited to, the use of antibodies directed to CD2, CD3, CD4, CD5, and/or CD8.

T cells can be co-cultured with dendritic cells exposed to the predetermined antigen as a mixed T cell population or as a purified T cell subset. For example, purified $CD8^+$ T cells can be co-cultured with antigen-exposed dendritic cells to elicit an antigen-specific CTL. In certain embodiments, early elimination of $CD4^+$-T cells can prevent the overgrowth of $CD4^+$ cells in a mixed culture of both $CD8^+$ and $CD4^+$ T cells. Alternatively, mixed populations of $CD4^+$ and $CD8^+$ T cells can be co-cultured with dendritic cells to elicit a response specific to an antigen encompassing both a cytotoxic and $T_H$ immune response.

Such stimulated T cells optionally can be reinfused into a subjects. (See, e.g., Riddle and Greenberg, *J. Antimicrobial Chemotherapy* 45:35-43, 2000; Correale et al., *J. Neuroimmunology* 107:130-39, 2000; the disclosures of which are incorporated by reference herein.) For example, immature dendritic cells can be contacted with antigen (e.g., PSMA) and matured to form mature dendritic cells. T cell can be isolated from a subject, contacted with the mature dendritic cells ex vivo, and then re-administered to the subject. For example, doses of about $1 \times 10^7$ to about $5 \times 10^9$ $CD8^+$ T cells can be administered to a subject weekly, or bi-weekly, for a period of 1-4 months, or more. Alternatively, the mature dendritic cells can be administered directly to the subject. Typically, about $1 \times 10^7$ dendritic cells are used per administration to a patient.

Typically a leukaphoresis product from a donor treated with a stem cell mobilization agent comprises about 1 to 5% cells, about 5 to about 20% granulocytes, about 40 to about 60% lymphocytes around about 10 to about 25% monocytes with significant amounts of red blood cells and platelets. Using a TFF device of the present invention with a filter having a pore size of about 3 to about 5.5 microns results in an enriched leukocyte population comprising about 60 to about 70% monocytes, almost no granulocytes, about 10% lymphocytes and about 10 to about 40% $CD 34^+$ cells. This enriched leukocytes population can be used as set forth below.

In other embodiments, the methods of the present invention are used to obtain a cell subset other than monocytes or monocytic dendritic cell precursors. For example, an enriched population of leukocytes can be used as a source of hematopoietic stem cells for, e.g., allogeneic or autologous transplantation. In particular embodiments, the enriched population of leukocytes is further enriched for the stem cells following the tangential flow separation procedure. Methods for enrichment of hematopoietic stem cells from a source of peripheral blood leukocytes are known in the art and can be adapted for use with an enriched population of leukocytes isolated as described herein. For example, an enriched population of leukocytes can be further enriched for $CD34^+$ cells using, e.g., immunomagnetic separation techniques (see, e.g., Rowley et al., *Bone Marrow Transplant.* 21:1253, 1998; Denning-Kendall et al., *Br. J. Haematol.* 105:780, 1999). In addition, to further increase stem cell yields, a cell population enriched in monocytes subsequent to TFF as described in the present invention can be cultured in the presence of, for example, about 50 ng/ml M-CSF in medium containing fetal serum to derive $CD34^+$ cells. The culture must be carried out in a non-adhesive cell culture container such as a TEFLON® culture bag. Further, peripheral blood donors can be subjected to a stem cell mobilizing regimen prior to collection of peripheral blood and separation of leukocytes by TFF. Various mobilizing agents for increasing efficiency of stem cell harvest are known in the art. For example, donors can be treated with GM-CSF, G-CSF, AMD3100 (or other agent that inhibits CXCR-4 function), and/or mobilizing chemotherapeutic agents such as, e.g., high- or low-dose cyclophosphamide (see, e.g., Deliliers et al., *Leuk. Lymphoma,* 43:1957, 2002). The blood donor can be the patient to receive the transplant, a close relative, a HLA-matched individual, or the like.

In yet another embodiment, the methods of the present invention are also used to obtain a non-stem cell subset such as, for example, a cell population enriched in progenitor cells (e.g., hematopoietic or endothelial progenitor cells) or cells that secrete a factor of interest (e.g., hematopoietic or angiogenic growth factors). For example, circulating endothelial progenitor cells (CEPs) can be identified as a subset of circulating $CD34^+$ cells by, e.g., coexpression of VEGFR-2 and AC133 (as well as, e.g., VE-cadherin and E-selectin). (See, e.g., Peichev et al., *Blood* 95:952, 2000.) An enriched population of leukocytes can be further enriched for CEPs using, for example, immunomagnetic separation techniques with antibodies directed to VEGFR-2 and AC133. Also, CEPs can be mobilized prior to TFF by treatment with cytokines such as, e.g., VEGF. (See, e.g., Gill et al., *Circ Res.,* 88:167, 2001). Further, in yet other embodiments, endothelial-like circulating angiogenic cells (CACs) (which secrete, e.g., VEGF, HGF, G-CSF, and GM-CSF) are obtained by culturing an enriched population of leukocytes with, e.g., VEGF, bFGF, IGF-1, EGF, and FBS on a fibronectin-coated surface and then discarding non-adherent cells (see, e.g., Rehman et al., *Circulation* 107:1164, 2003).

In addition, the enriched population of leukocytes can be cultured to induce expansion of pluripotent progenitor or stem cells. For example, $CD34^+$ stem cells can be expanded by culture with hematopoietic growth factors such as, e.g., a combination IL-1, IL-3, IL-6, stem cell factor (SCF), granulocyte-monocyte colony-stimulating factor (GM-CSF) and G-CSF (see, e.g., Sun et al., *Haematologica* 88:561, 2003). Alternatively, for example, a population enriched for monocytes can be treated with, e.g., M-CSF, LIF, and/or IL-6 to obtain pluripotent "f-macrophages" (f-MΦ), which morphologically resemble fibroblasts and, unlike standard macrophages, display elevated levels of CD34 (See Zhao et al., *Proc. Natl. Acad. Sci. USA* 100:2426, 2003.) The progenitor or stem cells can subsequently be treated with any of various cytokines and growth factors to induce differentiation into hematopoietic or non-hematopoietic lineages.

In other embodiments, an enriched population of leukocytes can be cultured under conditions suitable for inducing differentiation (e.g., differentiation of progenitor cells or transdifferentiation of more differentiated cells types such as, for example, monocytes or monocyte-derived dendritic cells). (As used herein, "transdifferentiation" refers to a processs of phenotypic modulation of a differentiated cell, generally without the need for any cell division, whereby the differentiated cell differentiates into a morphologically and/or functionally different cell type.) For example, in addition to differentiation into dendritic cells, monocytes can be transformed into other hematopoietic or non-hematopoietic cell types, including, e.g., macrophages, osteoclasts, and endothelial-like cells, depending on culture conditions (see, e.g., Becker et al., *J. Immunol.* 139:3703, 1987; Nicholson et al., *Clin Sci.* 99:133, 2000; Havemann et al., in *Novel Angiogenic Mechanisms: Role of Circulating Progenitor Endothelial Cells* 47-57 (Nicanor I. Moldovan eds., 2003)). In one embodiment, an enriched population of monocytes or monocyte-derived dendritic cells is transdifferentiated into endothelial-like cells by culture with, e.g., VEGF, bFGF, IGF-1, hydrocortisone, and FCS on a fibronectin-coated surface. (See Havemann et al., supra.) Also, an enriched population of leukocytes can be cultured under conditions that induce differentiation of relatively undifferentiated cell subsets (e.g., pluripotent progenitor and stem cells) into hematopoietic or non-hematopoietic lineages using any of various cytokines or growth factors. For example, monocyte-derived pluripotent stem cells (f-MΦ) can be induced to differentiate into standard macrophages, T lymphocytes, epithelial cells, neuronal cells, endothelial cells, or hepatocytes by treatment with, e.g., LPS, IL-2, EGF, NGF, VEGF, or HGF, respectively. (See Zhao et al., supra) Such differentiation can be induced prior to or following cell expansion such as, for example, described supra.

The following examples are provided merely as illustrative of various aspects of the invention and should not be construed to limit the invention in any way.

EXAMPLE 1

TFF Device with Remover Unit and Recovery Unit in Loop Configuration

One embodiment of the present invention comprises a configuration having a remover unit (1) and a recovery unit (2) in a loop configuration of the tangential flow filtration device. (FIG. 1A) The remover unit included a housing having two chambers (a cross-flow chamber (3) and a filtrate chamber (4)), separated by a microporous filter (5) (142 mm in diameter) having a pore size of about 1 micron to about 10 microns. The cross-flow chamber included a fluid inlet (6) and a fluid outlet (7). The filtrate chamber included a filtrate outlet (8). The recovery unit included a housing (9) containing a return inlet (10), a return outlet (11), a sample inlet (12), and a solution inlet (13). In certain embodiments the sample inlet and solution inlet are the same, but can be separate. Sample (e.g. blood, blood preparations, or a prepared population of leukocytes) was introduced into the recovery unit by the sample inlet (12), and was withdrawn through the return outlet (11) to the remover unit by action of a recirculating pump (14). Sample was introduced into the remover unit through the fluid inlet (6) and flowed across the microporous membrane (5), such that the fluid's movement was directed at a tangent to the direction of filtration. The fluid inlet (6) was positioned generally perpendicular to the radius of the filter. The relative inlet, filtration and outlet rates induced a vortex, the center of which drew components in the blood preparation not passing through the filter, to the fluid outlet (7) and back to the recovery unit (2). The flow of fluid between the recovery unit and the remover unit was controlled by the recirculation pump (14). The removal of filtrate from the remover unit was controlled by a filtrate pump (15).

EXAMPLE 2

Figure 2:
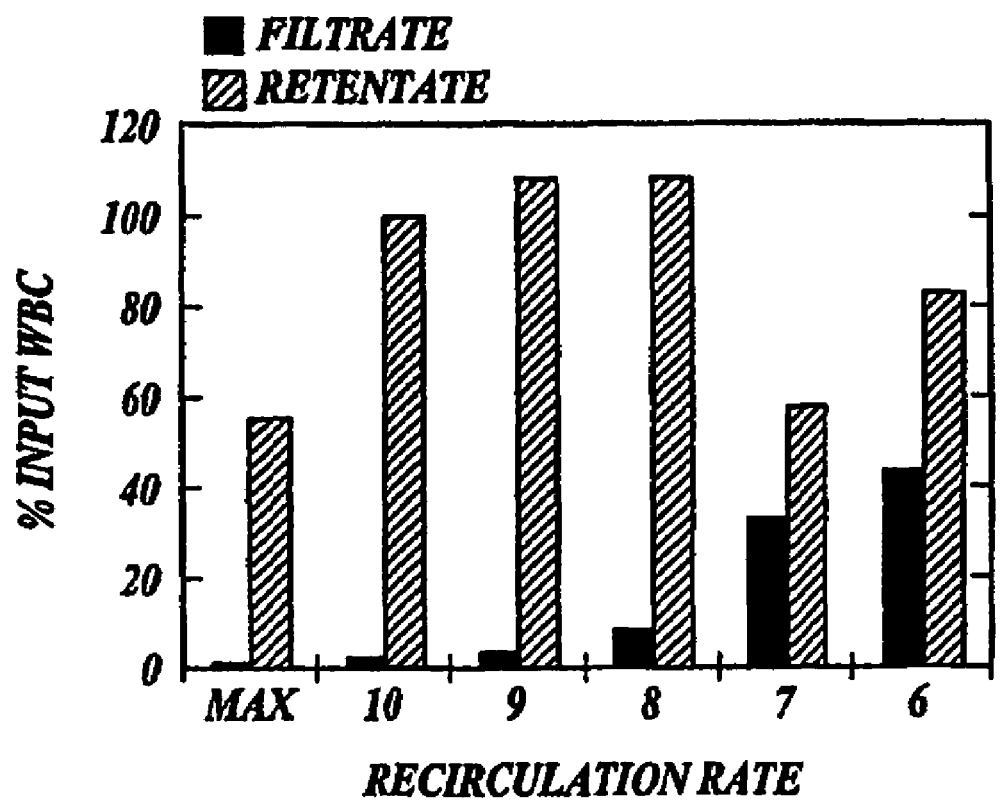
FIG. 2 depicts an example of tangential flow filtration (TFF) performed on samples of leukopheresis product under various conditions. Samples of 10 ml of leukopheresis product, diluted 1:5 in a buffer of PBS+heparin+DNase I were subjected to TFF using a 3 micron filter with a filtration rate of 15 ml/min. The percentage of leukocytes (WBC) in the retentate (designated "Retentate"; hatched bars) and filtrate (designated "Filtrate"; dark bars) after TFF are shown. The recirculation (input) rates for Max, 10, 9, 8, 7, and 6 corresponded to 1680, 1380, 1080, 870, and 540 ml/min, respectively.

Retention of Leukocytes Following TFF—Effects of Recirculation Rate and Filtrate Rate on Retention Efficiency In this example the enrichment of leukocytes using a TFF device as described in Example 1, which accommodated polyester membranes of 142 mm in diameter, was demonstrated. A sample of leukopheresis product was subjected to TFF in a device under various conditions, and the selective retention of leukocytes was assessed. In one set of studies, TFF was performed for 10 ml of leukopheresis product using a 3 micron filter, with a filtration rate of 15 ml/min (for 17 min) and at various recirculation (input) rates (e.g., 1680, 1380, 1080, 870, and 540 ml/min). Most of the leukocytes were generally retained in the retentate (i.e., less than about 10 percent of the leukocytes in the filtrate) unless the recirculation rate was lower than 1080 ml/min (FIG. 2; note: the corresponding actual recirculation rates designated Max, 10, 9, 8, 7, and 6 were 1680, 1380, 1080, 870, and 540 ml/min, respectively).

Figure 3:
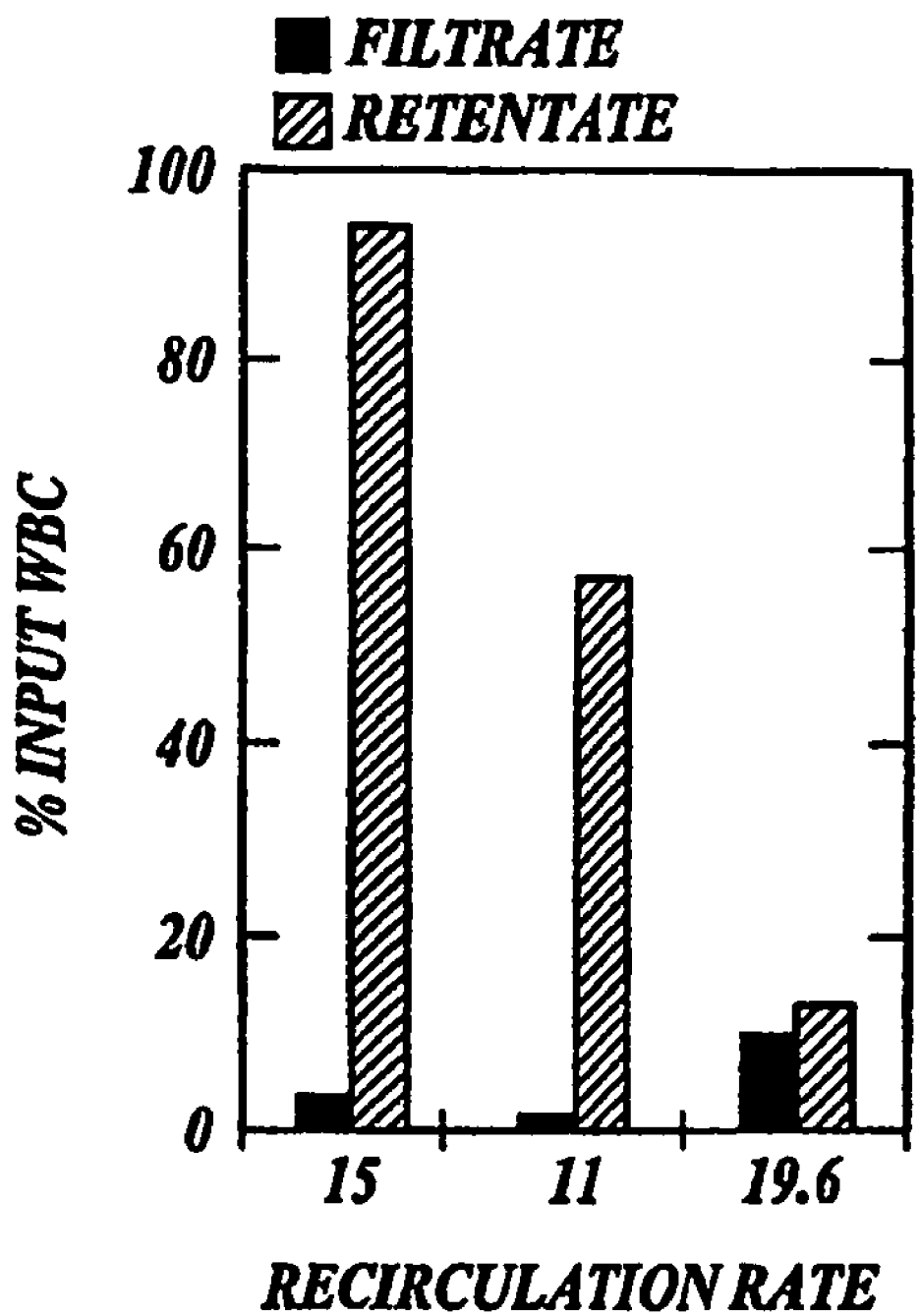
FIG. 3 depicts the results of a study of TFF performed on leukopheresis product in a TFF device using a 3 micron filter, with a recirculation (input) rate of 1080 ml/min at three different filtration rates (11, 15, and 19.6 ml/min). The percentage of leukocytes (designated "WBC") in the retentate (hatched bars) or filtrate (designated "Filtrate"; dark bars) is shown.

In another set of studies, TFF was performed for 10 ml of leukopheresis product in the TFF device of Example 1 using a 3 micron filter, with a recirculation (input) rate of 1080 ml/min at three different filtration rates (11, 15, and 19.6 ml/min). About 250 ml of filtrate was collected per study. Neither the 19.6 ml/min nor the 11 ml/min filtration rate was substantially more beneficial than the 15 ml/min filtration rate for retention of leukocytes (FIG. 3).

EXAMPLE 3

Selective Removal of Erythrocytes From Leukopheresis Product

Figure 4:
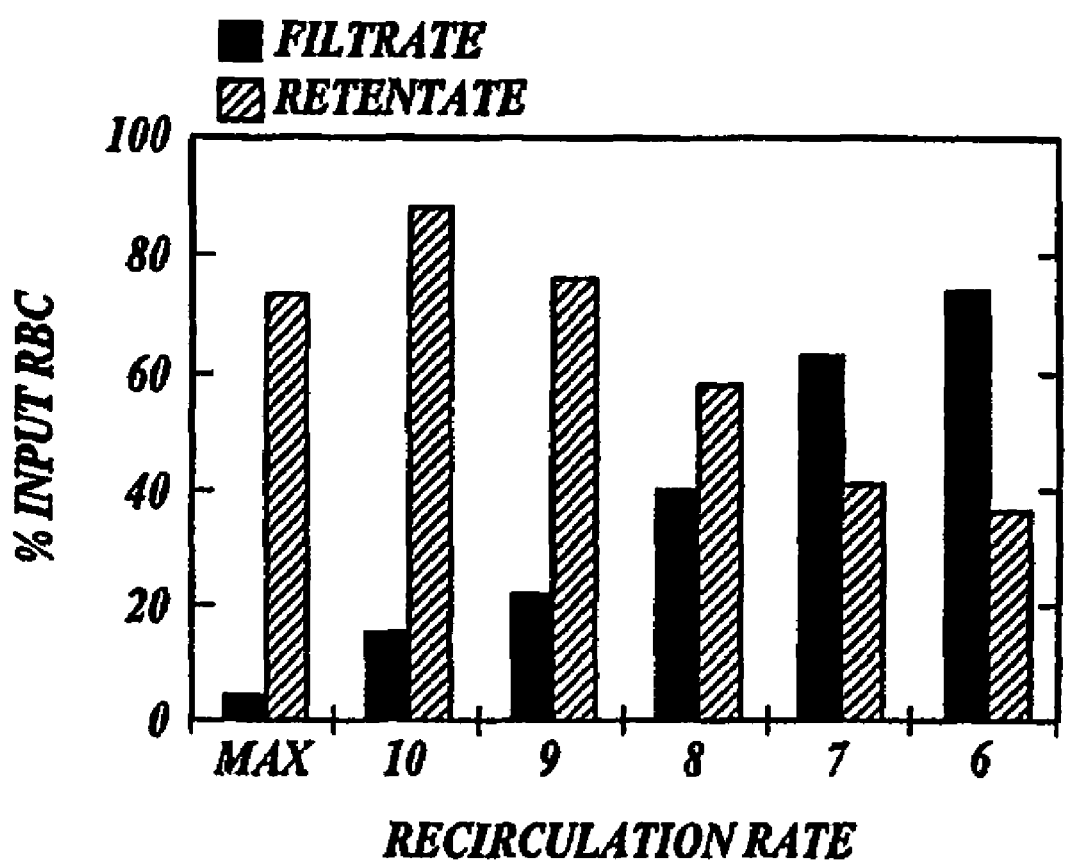
FIG. 4 depicts additional results of TFF performed on samples of leukopheresis product for the study described in FIG. 1. Samples of 10 ml of leukopheresis product, diluted 1:5, were subjected to TFF using a 3 micron filter with a filtration rate of 15 ml/min. The percentage of erythrocytes (designated "RBC") in the retentate (hatched boxes) and filtrate (dark boxes) after TFF are shown. The recirculation (input) rates for Max, 10, 9, 8, 7, and 6 corresponded to 1680, 1380, 1080, 870, and 540 ml/min, respectively.

In this example the selective removal of erythrocytes and the effects of recirculation rate, filtration rate and sample concentration on the separation efficiency using the TFF device of Example 1 was demonstrated. Samples of leukopheresis product were subjected to TFF under the conditions as established in Example 2, and the selective removal of erythrocytes was assessed. As in Example 2, TFF was performed for 10 ml of leukopheresis product using a 3 micron filter, with a filtration rate of 15 ml/min (for 17 min) and at various recirculation (input) rates (e.g., 1680, 1380, 1080, 870, and 540 ml/min). It was determined that generally, reducing the recirculation rate promoted more erythrocytes to pass into the filtrate (FIG. 4; note: the corresponding actual recirculation rates for Max, 10, 9, 8, 7, and 6 were 1680, 1380, 1080, 870, and 540 ml/min, respectively). It can be seem that while decreasing the recirculation rate did increase the removal of erythrocytes from the retentate, at a recirculation rate lower than 1080 ml/min the yield of leukocytes in the retentate was reduced (FIG. 4).

Figure 5:
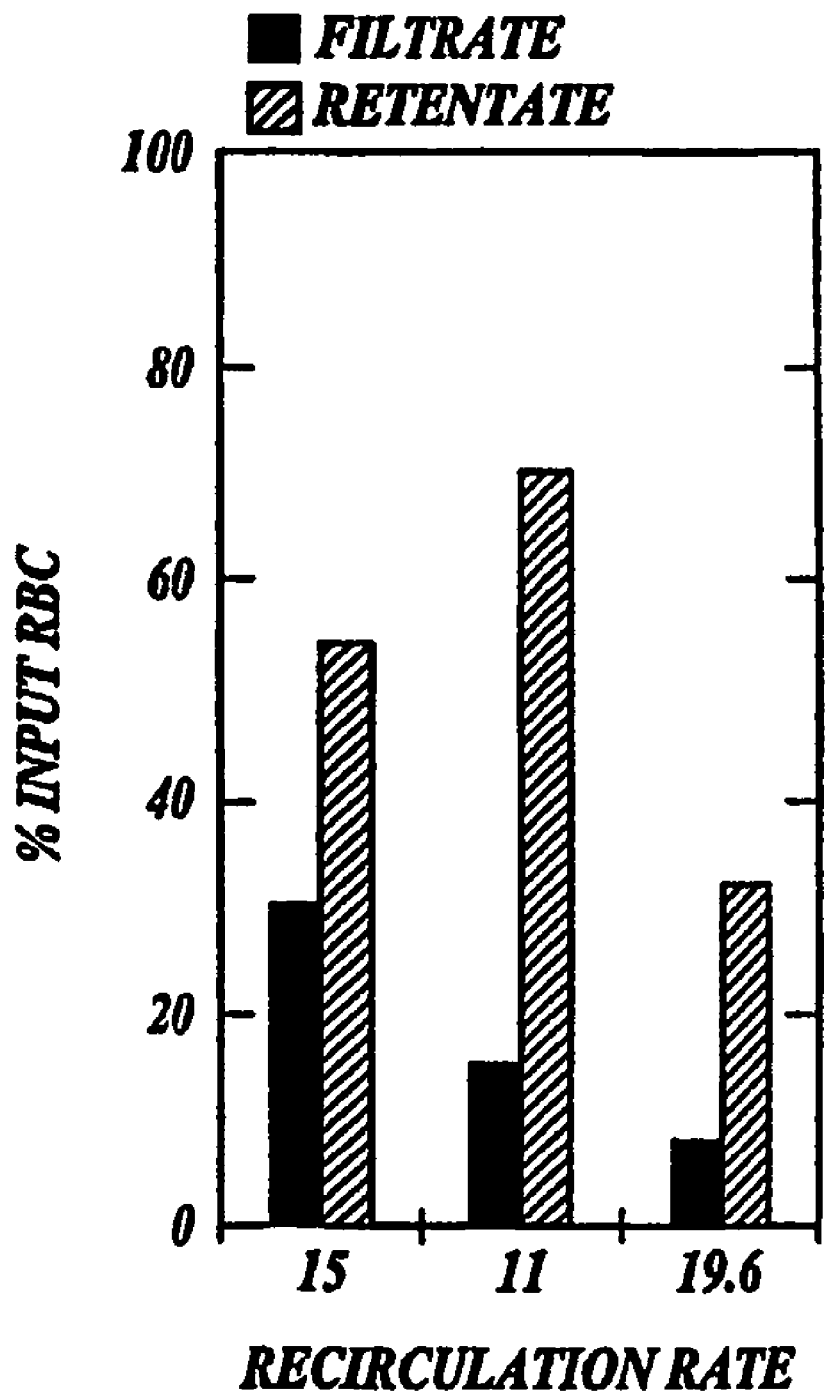
FIG. 5 depicts additional results of TFF performed on samples of leukopheresis product for the study described in FIG. 2. Samples of 10 ml of leukopheresis product, diluted 1:5, were subjected to TFF using a 3 micron filter, with a recirculation (input) rate of 1080 ml/min at three different filtration rates (11, 15, and 19.6 ml/min). The percentage of erythrocytes (designated "RBC") in the retentate (hatched bars) or filtrate (designated "Filtrate"; dark bars) is shown.

As in Example 2, TFF was performed for 10 ml of leukopheresis product in the same TFF device using a 3 micron filter, with a recirculation (input) rate of 1080 ml/min at three different filtration rates (11, 15, and 19.6 ml/min). About 250 ml of filtrate was collected per study. Neither the 19.6 ml/min nor the 11 ml/min filtration rate was substantially more beneficial than the 15 ml/min filtration rate for the selective removal of erythrocytes (FIG. 5). The filtration rate of 19.6 ml/min reduced the erythrocytes in the retentate more than 15 ml/min, but as seen in Example 2 the 15 ml/min filtration rate resulted in a greater yield of leukocytes in the retentate (FIG. 3).

Figure 6:
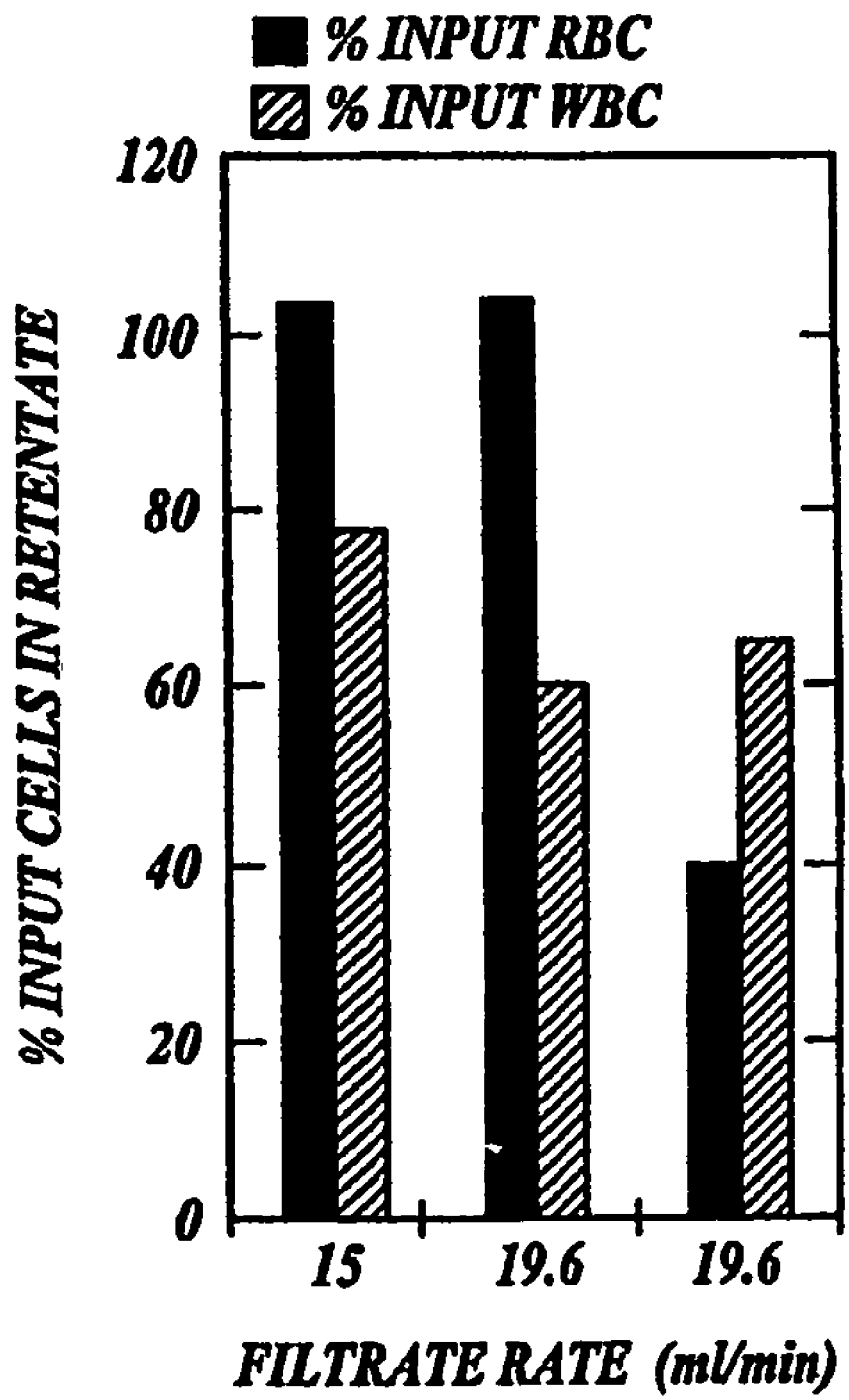
FIG. 6 depicts an example of the effects of increasing the concentration of leukopheresis material in the sample. 50 ml of leukopheresis material, diluted 1:5 in PBS+heparin+ DNase I, was subjected to TFF using a device having a 3 micron pore size filter. The percentage of erythrocytes (designated "RBC") and leukocytes (designated "WBC") in the retentate (designated "Retentate") is shown as a function of the filtration rate.

Referring to FIG. 6, the effect of increasing the concentration of leukopheresis material in the sample was also studied. Fifty ml (50 ml) of leukopheresis material, diluted 1:5 in PBS+heparin+DNase I, was subjected to TFF using a device with a filter having a 3 micron pore size. The percentage of erythrocytes (designated "RBC") in the retentate was about the same, about 100% of input, if the filtration rate was about 15 ml/min or 19.6 ml/min. However, if the 50 ml of leukopheresis product was diluted 1:2 in the same buffer, only 40% of the input erythrocytes were retained in the retentate, showing that loading of higher sample concentrations can also promote the separation of erythrocytes from leukocytes (designated "WBC").

EXAMPLE 4

Figure 7:
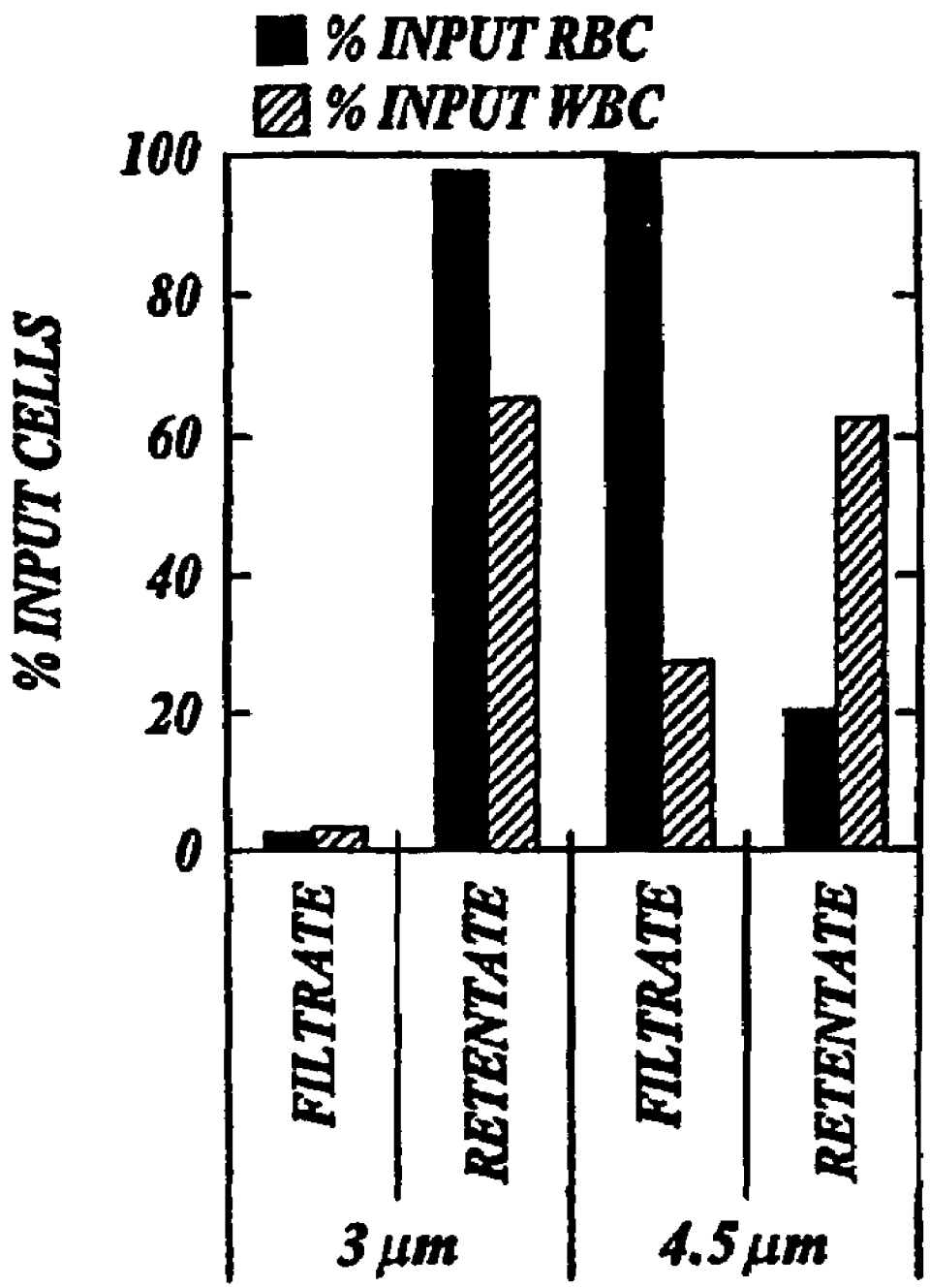
FIG. 7 depicts an example of the separation of leukopheresis product between 3 micron and 5 micron filters upon scale-up of leukopheresis product (120 ml or ½ of an entire unit). The recirculation (input) rate was 1680 ml/min, and the filtration rate was 15 ml/min. For TFF performed using a 5 micron filter, about 80% of the erythrocytes (designated "RBC"; dark shaded bars) were removed from the retentate, while about 62% of input leukocytes (designated "WBC"; light hatched bars), or greater than about 70% of input monocytes, were retained. In contrast, using the 3 micron filter, about 65% of input leukocytes were retained in the retentate, but only 3% of the erythrocytes were removed.

Selective Removal of Erythrocytes from Leukopheresis Product—Effect of Pore Size on Removal of Erythrocytes To confirm that the embodiment of the TFF device set forth in Example 1 would perform similarly upon scale-up, TFF of 120 ml of leukopheresis product (½ of an entire unit) was compared in devices having filters with a pore size of 3 micron verses 4.5 micron. The recirculation (input) rate was 1680 ml/min, and the filtration rate was 15 ml/min. Referring to FIG. 7, for TFF performed using a 4.5 micron filter, about 80% of the erythrocytes (designated "RBC"; dark shaded bars) were removed from the retentate, while about 62% of input leukocytes (designated "WBC"; light hatched bars), or greater than about 70% of input monocytes, were retained. In contrast, using the 3 micron filter, about 65% of input leukocytes were retained in the retentate, but only 3% of the erythrocytes were removed.

Figure 8:
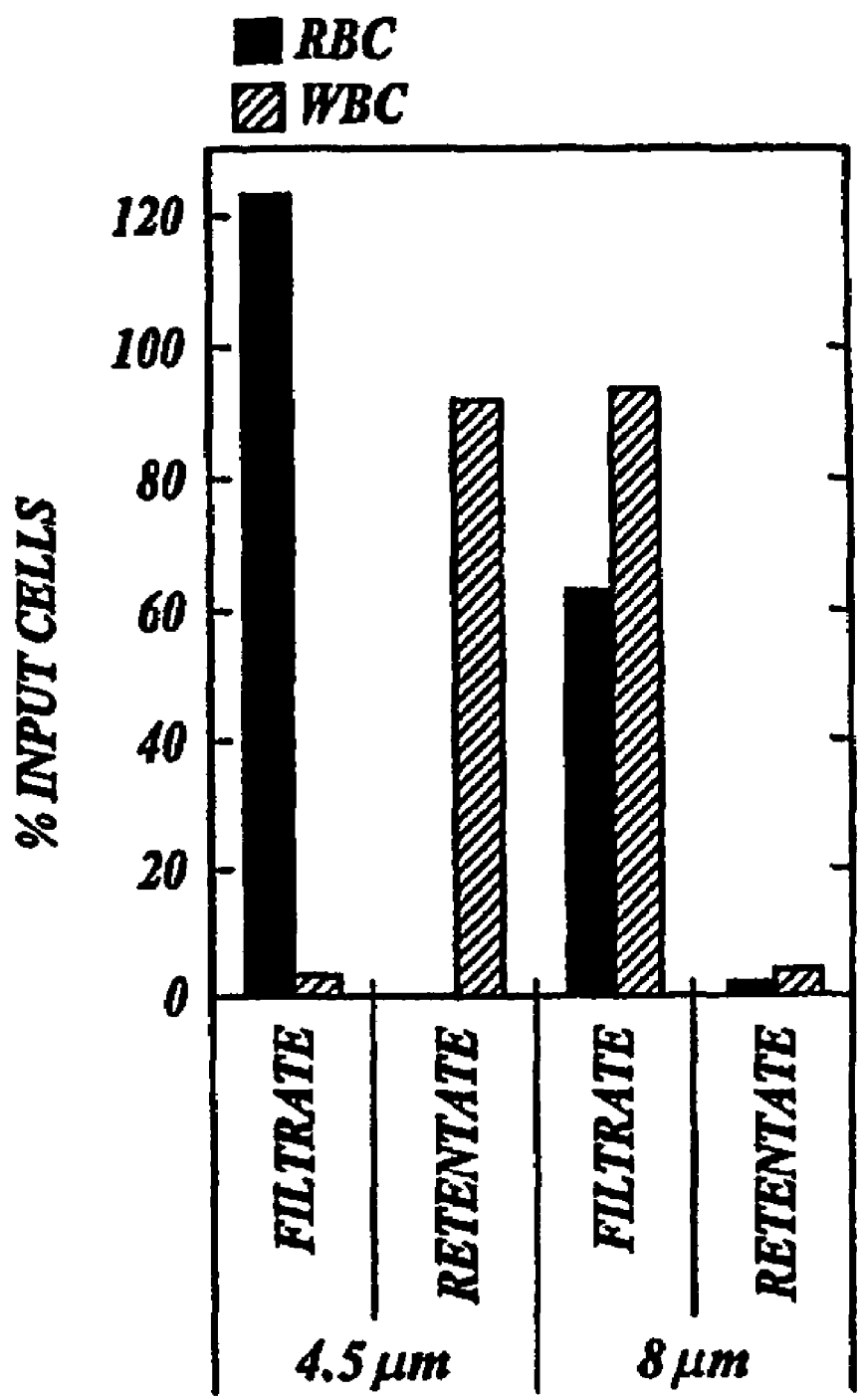
FIG. 8 depicts a comparison of the separation of leukopheresis product through an approximately 4.5 micron and 8 micron filters upon scale-up of the quantity of leukopheresis product provided as the sample. The recirculation (input) rate was 1680 ml/min, the filtration rate was 15 ml/min. For TFF performed using a 4.5 micron filter, about 99% of the erythrocytes (designated "RBC"; dark shaded bars) were removed from the retentate, while about 90% of input leukocytes (designated "WBC"; light hatched bars) were retained. In contrast, the 8 micron filter, about 98% of input erythrocytes were removed, but only 4% of the leukocytes were retained.

Referring to FIG. 8, TFF of 45 ml of leukopheresis product was compared in devices having filters with a pore size of 4.5 micron versus 8 micron. The recirculation (input) rate was 1680 ml/min, the filtration rate was 15 ml/min, and the time was 60 min. For TFF performed using a 4.5 micron filter, about 99% of the erythrocytes (designated "RBC"; dark shaded bars) were removed from the retentate, while about 90% of input leukocytes (designated "WBC"; light hatched bars) were retained. For the 8 micron filter, about 98% of input erythrocytes were removed, but only 4% of the leukocytes were retained, showing that using a 4.5 micron filter promoted equal removal of erythrocytes to the larger 8 micron pore size filter, but a better retention of leukocytes (designated "WBC") was obtained.

EXAMPLE 5

Selective Enrichment of Leukocytes with Removal of Platelets and Plasma

In this example samples of leukopheresis product were subjected to TFF in the device described in Example 1 under various conditions, and the selective removal of platelets and plasma was assessed. Referring to Table 1, experiments 1 to 6, 45 ml of leukopheresis product was subjected to TFF with a filter having either a 4.5 micron or a 8 micron pore size, the recirculation rate (input rate) was either 1690 or 1880 ml/min, and the filtration rate was 15 ml/min. The filtration was carried out for either 60 or 90 min as indicated. Following TFF, the retentate was assayed for leukocytes, platelets, and plasma. In all experiments, between 92 to about 100% of the input platelets and about 97 to about 99% of the input plasma were removed from the retentate, independent of pore size (4.5 micron or 8 micron), recirculation (input) rate (1690 or 1880 ml/min), and time (60 min or 90 min). For experiment 7, an entire leukopheresis product (250 ml) was subjected to TFF using a 4.5 micron pore size, 1690 ml/min recirculation (input) rate, 15 ml/min filtration rate, for a 90 min duration. Following TFF, the retentate was assayed and found to have about 84% of the input leukocytes, but only 2% of the input platelets and 3% of the input plasma.

TABLE 1

Effect of Filter Pore Sizes on Retention of PBMC

|  | Leukoperesis Input | Pore Size | Recirculation Rate | Time | % Input WBC in Retentate | % Input Platelets in Retentate | % Input Plasma in Retentate |
|---|---|---|---|---|---|---|---|
| Exp 1 | 45 ml | 4.5 μm | 1690 ml/min | 60 min | 88 | 2.0 | 2.0 |
| Exp 2 | 45 ml | 4.5 μm | 1690 ml/min | 60 min | 67 | 8.0 | 2.0 |
| Exp 3 | 45 ml | 4.5 μm | 1690 ml/min | 60 min | 79 | 3.0 | 1.0 |
| Exp 4 | 45 ml | 4.5 μm | 1888 ml/min | 60 min | 92 | 0.0 | 1.0 |
|  | 45 ml | 8 μm | 1888 ml/min | 60 min | 4 | 0.0 | 1.0 |
| Exp 5 | 45 ml | 4.5 μm | 1690 ml/min | 60 min | 130 | 3.0 | 3.0 |
|  | 45 ml | 4.5 μm | 1880 ml/min | 60 min | 47 | 3.0 | 2.0 |
| Exp 6 | 45 ml | 4.5 μm | 1690 ml/min | 60 min | 80 | 1.0 | 2.0 |
|  | 45 ml | 4.5 μm | 1690 ml/min | 90 min | 72 | 0.2 | 2.0 |
| Exp 7 | 250 ml | 4.5 μm | 1690 ml/min | 90 min | 84 | 2.0 | 3.0 |

These experiments show that TFF removes most of the platelets and plasma for multiple pore sizes (4.5 micron or 8 micron), recirculation (input) rates (1690 or 1880 ml/min), volumes of leukopheresis sample (45 ml to 250 ml), and time (60 min to 90 min).

EXAMPLE 6

Selective Enrichment of Leukocytes from Whole Leukopheresis Products

Figure 9:
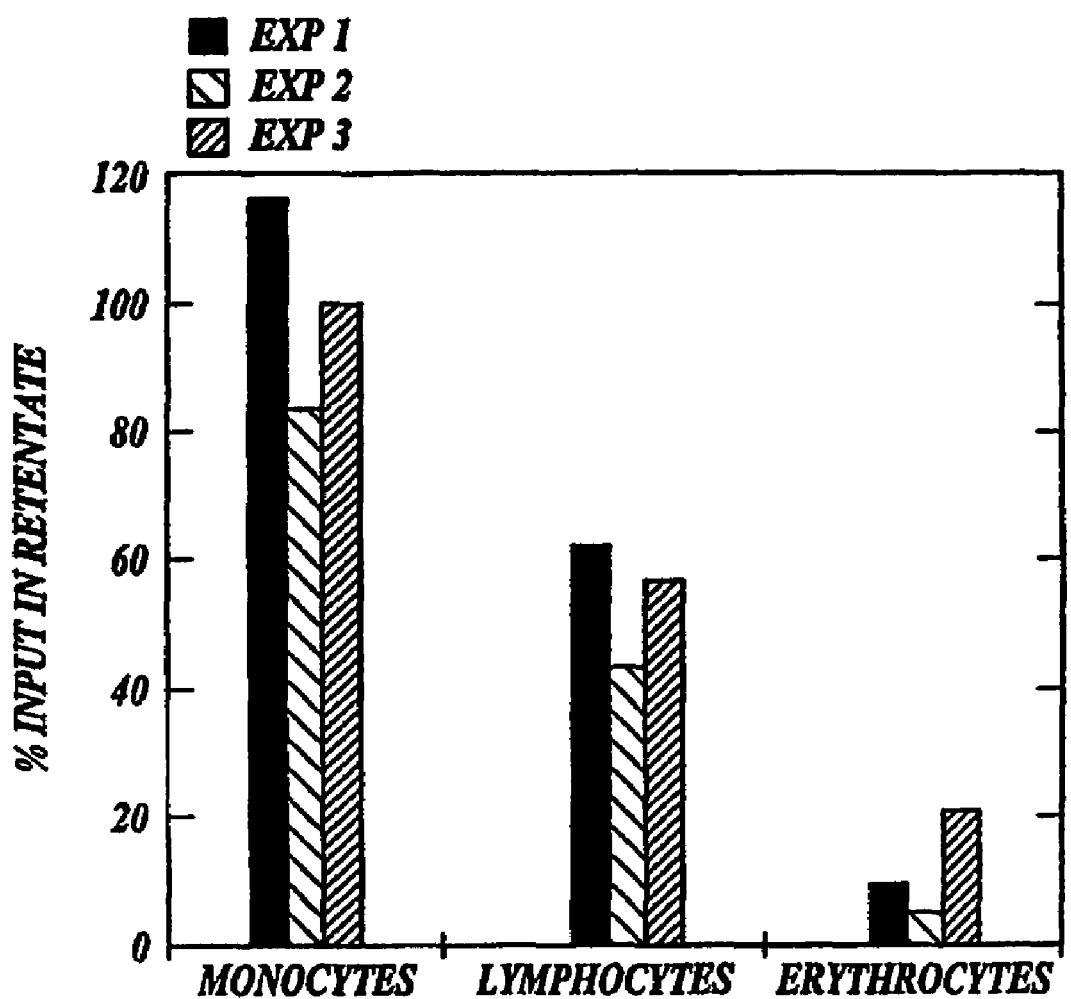
FIG. 9 depicts an example of the separation on 4.5 micron filters upon scale-up of leukopheresis product processed (250 ml or an entire unit). The recirculation (input) rate was 1680 ml/min, and the filtration rate was 15 ml/min. For TFF on 4.5 micron filters performed for 90 min on three different leukopheresis products, between 80 to 95% of the erythrocytes were removed from the retentate, while about 80 to 100% of input monocytes were retained. Following TFF of one leukopheresis sample, the retentate was also assayed and found to have about only 2% of the input platelets and 3% of the input plasma (designated Exp 7 in Table 1).

To confirm that this embodiment of the TFF device would perform reproducibly upon scale-up to larger sample sizes, a TFF device designated a 5× device was used with 250 ml of leukopheresis product (an entire unit) using a 4.5 micron pore size filter, a recirculation rate of 1680 ml/min, and a filtration rate of 15 ml/min and compared with the lower input volume. Referring to FIG. 9, TFF was performed for 90 min on three different leukopheresis products on different days. Between 80 to 95% of the erythrocytes were removed from the retentate, while about 80 to about 100% of input monocytes were retained. Following TFF for Exp 1 in FIG. 9, the retentate was also assayed and found to have about only 2% of the input platelets and 3% of the input plasma (designated Exp 7 in Table 1). These data demonstrated that TFF can reproducibly enrich for leukocytes and preferentially remove erythrocytes, platelets, and plasma from the retentate.

EXAMPLE 7

TFF Device for Selectively Enriching a Blood Preparation for Monocytes

In addition to enrichment for leukocytes, selective enrichment of monocytes from blood preparations was tested using a TFF apparatus. This particular embodiment of the device comprised an inverted ("type IV") configuration designed to change the flow dynamics by altering the direction of gravitational force across the membrane (FIG. 1C). Two hundred thirty-five (235) ml of leukopheresis product was subjected to TFF for 90 minutes using a 4.5 micron pore size filter, a recirculation (input) rate of 1680 ml/min, and a filtration rate of 15 ml/min. After 60 minutes of TFF, in order to increase the effective filtrate, the void volume was reduced to about 120 ml. The input, retentate, and filtrate were each assayed for cell content. Whereas the input had 32% monocytes and 65% lymphocytes, the retentate was found to have about 71% monocytes compared to 22% lymphocytes. The filtrate contained 1.5% monocytes compared to 83% lymphocytes. (See Table 2).

TABLE 2

Enrichment of Monocytes Using Type IV (Inverted) TFF Configuration

|  | Input | Retentate | Filtrate |
| --- | --- | --- | --- |
| Monocyte No.(×$10^9$) | 2.85 | 1.37 | 0.861 |
| Lymphocyte No. (×$10^9$) | 5.67 | 0.428 | 4.86 |
| Granulocyte No. (×$10^9$) | 0.133 | 0.0571 | 0.0797 |
| RBC No. (×$10^9$) | 64.6 | 1.37 | 78.9 |
| WBC No. (×$10^9$) | 8.78 | 1.93 | 5.86 |
| % Monocytes | 32.46 | 71.1 | 14.7 |
| % Lymphocytes | 64.54 | 22.17 | 82.88 |
| % Granulocytes | 0.0151 | 2.96 | 1.36 |
| Unlysed (×$10^9$) | 73.4 | 3.30 | 84.8 |

EXAMPLE 8

Generation of Dendritic Cells From Cells Isolated by TFF

In this example the cell population that was isolated and purified by TFF was cultured in standard conditions for the maturation of dendritic cells from monocytic dendritic precursor cells. The population of cells isolated by TFF contained approximately 58.6% monocytes, 22% lymphocytes and 12.5% granulocytes. This mixture of cells was introduced into a tissue culture bag in X-Vivo15 media and 500 U each of IL-4 and GM-CSF. After five days, approximately 50% of the cells were harvested, stained for DC markers and analyzed by flow cytometry. The other approximately 50% of the cells were exposed to maturation agents, BCG (2.8×$10^5$ pfu/ml) and IFNγ (1000 U/ml). After 24 h those cells were also harvested and analyzed in the same manner. Table 3 shows the results of these analyses. The values provided represent the percentage of positive cells among the dendritic cells, i.e., after gating on large cells.

TABLE 3

Detection of Cell Surface Markers on Immature and Mature Dendritic Cells.

| Marker | Immature DC (% positive) | Mature DC (% positive) |
| --- | --- | --- |
| CD14 | 10 | 2 |
| CD11c | 99 | 96 |
| CD1a | 70 | 69 |
| CD80 | 75 | 74 |
| CD83 | 7 | 34 |
| CD86 | 90 | 89 |
| CD54[1] | 100 | 98 |
| MHC II[1] | 56 | 72 |

[1]These markers show a significant increase in mean fluorescence intensity (MFI) among positive cells after maturation Based on the forward light scatter and side scatter parameters of the flow-cytometric analysis it was determined that the immature dendritic cell population contained approximately 71% live DC, 21% lymphocytes and 7% other cells (mostly dead cells of unknown origin). The mature dendritic cell population contained 61% live DC, 21% lymphocytes and 15% other cells. These results demonstrated that monocytes purified directly from leukopheresis material by TFF can be efficiently converted into DC using standard culture conditions maturing dendritic cells.

EXAMPLE 8

Isolation of Monocytes on Glass Beads

An enriched population of leukocytes is isolated by TFF according to any of the previous examples. During TFF, the buffer is replaced with AIM-V media (Gibco-Life Science) containing 1% heat-inactivated autologous plasma (binding media). Glass beads (20 grams) are prepared by washing twice in binding media and are subsequently placed in a 60 milliliter syringe fitted with a frit to retain the beads to form a column bed. (Alternatively, Plastic Plus microcarrier beads (treated styrene copolymer beads from SoloHill Engineering, Inc.) or HilleX microcarrier beads (styrene copolymer beads from SoloHill Engineering, Inc.) can be used. The binding media is then drained from the column bed by gravity flow. The enriched population of leukocytes from TFF is applied to the column, and any flowthrough is collected. Binding media is added to provide a small layer of liquid above the column bed. The column with cells is incubated at 37° C. for 30 minutes.

After incubation, the column port is opened, and the flowthrough is collected. The column bed is then washed six times with binding media (35 ml/wash) administered and removed multiple times through the column port to allow gentle resuspension of the beads. These washes are followed by two washes with phosphate buffered saline ("PBS"). Cell counts are obtained for all washes and the original flow through, and they are analyzed by forward and side scatter FACS analysis to determine the percentage of monocytes present. After completing the washes, the bound monocytes are eluted from the beads using PBS/0, 4% EDTA (w/v), followed by one more PBS wash. The cells that are obtained in these fractions are analyzed in the same manner as the washes. The fractions rich in monocytes are pooled.

EXAMPLE 9

Differentiation of Dendritic Cells From Monocytes Eluted from Glass Beads

Monocytes are washed two times with 30 ml of PBS, and resuspended in culture media (X-VIVO 15 (Biowhittaker Corp.) with 500 U GM-CSF/ml and 500 U Interleukin 4/ml). A portion (⅔) of the cell suspension is then transferred to a rotary bioreactor (Synthecon) and cultured for 6 days at 37° C. in a humidified environment containing 5% $CO_2$. After culturing, the cell population comprises about 70% immature dendritic cells, based on cell size, granularity and cell surface markers.

EXAMPLE 10

Activation of Immature Dendritic Cells with Prostate Specific Antigen

Monocytes are isolated from a prostate cancer patient as described in the previous examples. The monocytes are cultured in tissue culture bags in X-VIVO 15 tissue culture media supplemented with GM-CSF and Interleukin 4 (500 U/ml each) for 6 days at 37° C. The resulting immature dendritic cells are then exposed to prostate specific antigen (PSMA) (isolated as described in U.S. Pat. No. 5,788,963) added to the culture media. The immature dendritic cells are then differentiated to form mature dendritic cells using a maturation agent. The mature (activated) dendritic cells are added to a T cell proliferation assay. T cell cultures are incubated in a humidified 37° C. incubator supplemented with 5% $CO_2$ for 5 days prior to addition of 1 µCi $^3$H-Thymidine/well of a microtiter plate. After a 24 hour incubation, the cells are harvested in a semi-automatic cell harvester (Skatron, Stevina, Va.), and the radioactivity of the collected cells is determined. T cell proliferation is assessed by measurement of average $^3$H-TdR incorporation.

EXAMPLE 11

Capacity of Cultured Mature Dendritic Cells to Present Antigen

To assess the capacity of the cultured, mature dendritic cells to present antigen to and stimulate autologous T cells from the same patients, T cell proliferation assays are conducted as described above (Example 10). Tetanus toxoid is chosen as the representative antigen in these experiments to determine whether patients' memory T cells can be activated in vitro. Autologous T cells cultured with the patient's dendritic cells and Tetanus toxoid will proliferate at levels significantly higher than background levels (in the absence dendritic cells) and at levels significantly higher than T cells cultured with mature (activated) dendritic cells without Tetanus toxoid (i.e., showing an autologous mixed lymphocyte reaction). Thus, the presentation of Tetanus toxoid by dendritic cells is useful for T cell proliferation.

EXAMPLE 12

Stimulation of Autologous T Cells

Mature (activated) dendritic cells specific for prostate cancer are used to stimulate autologous T cells of a prostate cancer patient. A crude cellular lysate of LNCaP cells, a metastatic prostate cancer cell line, is used as a representative prostate cancer antigen in a T cell proliferation assay generally as described in U.S. Pat. No. 5,788,963 (the disclosure of which is incorporated by reference herein). A significant increase in $^3$HTdR incorporation is observed when both mature activated dendritic cells and LNCaP lysates are included in the T cell cultures.

EXAMPLE 13

Administration of Stimulated Autologous T Cells to a Subject

T cells are prepared by leukopheresis from a subject. The T cells are contacted with mature activated dendritic cells. The dendritic cells are matured after contacting with a crude cellular lysate of LNCaP cells, a metastatic prostate cancer cell line. Following contacting, the T cells and dendritic cells are cultured and expanded. The expanded, activated T cells are administered to the subject at a dose of about $10^7$ to about $5 \times 10^9$ cells per dose.

EXAMPLE 14

Conversion of Monocytes to $CD34^+$ Stem Cells

The percentage of $CD34^+$ cells in peripheral blood is extremely low, ranging from about 0.01% to about 0.1%. $CD34^+$ cells are recognized as the cell type necessary for successful transplantation of hematopoietic function. Monocytes can be isolated from peripheral blood using the device and methods described above, yielding 1 to $2 \times 10^9$ monocytes. These cells can then be cultured in 50 ng/ml M-CSF in medium containing fetal bovine serum to derive $CD34^+$ cells. The cultures must be performed in a non-adhesive environment such as a TEFLON® culture bags. Cultures in standard polystyrene tissue culture flasks do not develop into $CD34^+$ cells. Analysis of the large cells in the culture revealed that the $CD34^+$ cell were found in the larger size range.

TABLE 4

Expression of CD34 on Monocytes after culture in M-CSF

|  | Percentage of $CD34^+$ Cells |
|---|---|
| Culture in culture bag | 21 |
| Gating on large cells | 58 |

TABLE 4-continued

Expression of CD34 on Monocytes after culture in M-CSF

| | Percentage of CD34+ Cells |
|---|---|
| Culture in flask | 6 |
| Gating on large cells | 11 |

CD34+ cells prepared by this method can be used transplantation to reconstitute the recipient's bone marrow or may be further cultured in the presence of other cytokines to generate endothelial cells for use in treating, eg. myocardial infarction, etc. and the like.

The examples are provided herein are intended to illustrate but not to limit the scope of the claimed invention. Other variants of the invention will be readily apparent to those of ordinary skill in the art and encompassed by the appended claims. All publications, patents, patent applications and other references cited herein and are also incorporated by reference herein.

What is claimed is:

1. A tangential flow filtration device for preparing a cell population enriched for leukocytes, comprising:
    a remover unit having a cross-flow chamber, a filtrate chamber and a filter disposed therebetween the filter having a retentate surface and a filtrate surface, the filter in fluid communication with the cross-flow chamber and the filtrate chamber;
    the cross-flow chamber having an inlet and an outlet, the inlet disposed to introduce the cell population comprising a sample of blood constituents comprising leukocytes into the cross-flow chamber and parallel to the retentate surface of the filter; and the outlet centrally disposed in a portion of the cross-flow chamber opposite the filter retentate surface;
    the filter having an average pore size ranging from about 1 to about 10 microns; such that flow of the sample of blood constituents across the filter enriches the cell population comprising the sample of blood constituents for leukocytes.

2. The device according to claim 1, further comprising:
    a means for providing a predetermined input rate of the sample to the inlet of the cross-flow chamber;
    a means for controlling a filtration rate of filtrate through the filter and into the filtrate chamber; and
    wherein the filtration rate controlling means limits the filtration rate to less than the unopposed filtration rate for the filter.

3. The device according to claim 1 or claim 2, wherein the filter pore size is about 3 microns to about 7 microns.

4. The device according to claim 1 or claim 2, wherein the filter pore size is about 3 microns to about 5.5 microns.

5. The device according to claim 1 or claim 2, further comprising: a source of the cell population comprising the blood constituents in fluid communication with the cross-flow chamber inlet.

6. The device according to claim 5, wherein the cell population comprising the source of blood constituents is a leukopheresis device.

7. The device according to claim 1 or claim 2, further comprising:
    a recovery unit comprising an inlet and an outlet, the cross-flow chamber and the recovery unit interconnected in loop format, wherein the cross-flow chamber inlet is in fluid communication with the recovery unit outlet, and the cross-flow chamber outlet is in fluid communication with the recovery unit inlet.

8. The device according to claim 7, wherein the recovery unit further comprises a sample inlet and a wash inlet.

9. The device according to claim 8, further comprising a source of replacement liquid in fluid communication with the wash inlet.

10. The device according to claim 9, wherein the replacement liquid is an isotonic buffer or tissue culture media.

11. The device according to claim 1 or claim 2, wherein the cross-flow chamber is cylindrical and the outlet is located opposite the center of the filter and perpendicular to a surface of the filter.

12. The device according to claim 1 or claim 2, further comprising a cell-processing apparatus in fluid communication with the remover unit.

13. The device according to claim 12, wherein the cell processing apparatus comprises beads.

14. The device according to claim 12, wherein the cell processing apparatus comprises a means for culturing the cell population enriched for leukocytes.

15. The device according to claim 14, wherein the means for culturing comprises:
    a vessel having a first port and a second port;
    a monocytic dendritic cell precursor adhering substrate, the substrate in fluid communication with the first port and the second port;
    a screen for retaining the substrate within the vessel, the screen having a pore size sufficient to allow passage of monocytic dendritic cell precursors and dendritic cells therethrough;
    a drain line in fluid communication with the first port; and
    a collection line in fluid communication with the first port.

16. The device according to claim 15, further comprising a plurality of fluid sources in fluid communication with the first port or the second port.

17. The device according to claim 15, further comprising a sealable tissue culture vessel adapted to aseptically receive the monocytic dendritic cell precursors.

18. The device according to claim 17, wherein the sealable tissue culture vessel is a tissue culture bag, flask or bioreactor.

19. The device according to claim 15, wherein the fluid sources comprise binding media, washing buffer and elution buffer.

20. The device according to claim 15, further comprising a pump in fluid communication with the plurality of fluid sources and the first port.

21. The device according to claim 15, further comprising:
    a temperature control means to maintain the substrate at a predetermined temperature.

22. The device according to claim 21, wherein the temperature controlling means is a heater.

23. A tangential flow device for enriching a cell population comprising a sample of blood constituents for leukocytes, comprising:
    a remover unit comprising a cross-flow chamber (3) and a filtrate chamber (4) separated by a filter (5), wherein the cross-flow chamber (3) has an inlet (6) and an outlet (7), the outlet centrally disposed in an upper portion of the chamber, and wherein the inlet is disposed above the filter and introduces fluid into the cross-flow chamber substantially parallel to the filter;
    a means for providing a predetermined input rate (14) of the cell population comprising the sample through the cross-flow chamber inlet; and
    a means for reducing a filtration rate (15) through the filter; wherein the filter has a pore size of about 3 microns to about 7 microns; and whereby the cell population comprising the sample is enriched for leukocytes in a retentate in the cross-flow chamber.

24. A tangential flow device for enriching cell population comprising a sample comprising blood constituents for leukocytes, comprising:
a remover unit (1) having a cross-flow chamber (3) and a filtrate chamber (4) separated by a filter (5), the cross-flow chamber having an inlet (6) and an outlet (7), the outlet disposed above the inlet and centrally disposed in an upper portion of the chamber, and wherein the filter is disposed below and substantially parallel to the cross-flow chamber inlet;
means for providing a predetermined input rate (14) of the sample through the cell population comprising the sample through the cross-flow chamber inlet;
means for providing a predetermined filtration rate (15) of the fluid through the filter, wherein the predetermined filtration rate is about one-fifth to about one one-hundredth of the predetermined input rate; and
means for providing a predetermined concentration of blood cells in the sample, wherein the predetermined concentration of blood cells is about $10^7$ to about $10^{10}$ cells per milliliter;
wherein the filter has pores having a pore size of about 3 microns to about 7 microns; and
whereby the sample is enriched for leukocytes in a retentate in the cross-flow chamber.

25. A method for separating leukocytes from a cell population comprising a sample of blood constituents from a subject wherein the sample comprises leukocytes, the method comprising:
(1) introducing the sample into a remover unit wherein the remover unit comprises a cross-flow chamber, a filtrate chamber and a filter disposed therebetween, the filter having a retentate surface and a filtrate surface, the filter in fluid communication with the cross-flow chamber and the filtrate chamber; the cross-flow chamber having an inlet and an outlet, the inlet disposed to introduce the cell population comprising the sample of blood constituents comprising the leukocytes from a source into the cross-flow chamber and parallel to the retentate surface of the filter, and the outlet centrally disposed in a portion of the cross-flow chamber opposite the filter retentate surface;
(2) subjecting the sample to cross-flow substantially parallel to a filter having a pore size of about 1 to about 10 microns;
(3) subjecting the fluid to filtration through the filter; and
(4) selectively removing non-leukocyte blood constituents from the sample through the filter and removing the leukocytes through the centrally disposed outlet to form a cell population enriched for leukocytes.

26. The method according to claim 25, further comprising: preparing the sample from the subject by leukopheresis, density centrifugation, differential lysis, filtration, or preparation of a buffy coat, for introduction in the remover unit.

27. The method according to claim 25, wherein the non-leukocyte blood constituents include plasma and platelets.

28. The method according to claim 25, wherein the non-leukocyte blood constituents include erythrocytes.

29. The method according to claim 25, wherein the leukocytes comprise monocytes.

30. The method according to claim 25, further comprising repeating steps (1), (2), and (3) at least two times to form cell population enriched for leukocytes.

31. The method according to claim 25, wherein the enriched cell population comprises at least about 20% leukocytes.

32. The method according to claim 25, wherein the enriched cell population comprises at least about 60% leukocytes.

33. The method according to claim 25, further comprising inducing a vortex motion of the sample in the cross-flow chamber.

34. The method according to claim 25, further comprising washing the cell population enriched for leukocytes with a wash solution.

35. A method for enriching a cell population comprising a sample of blood constituents for leukocytes, comprising:
(1) introducing the cell population comprising the sample into a tangential flow filtration (TFF) unit, the TFF unit comprising a cross-flow chamber, a filtrate chamber, and a filter in fluid communication with the cross-flow chamber and the filtrate chamber, the filter having a retentate surface and a filtrate surface, the cross-flow chamber having an inlet and an outlet, the inlet disposed to introduce the cell population comprising the sample of blood constituents comprising leukocytes from a source into the cross-flow chamber and parallel to the retentate surface of the filter, and the outlet centrally disposed in a portion of the cross-flow chamber opposite the filter retentate surface; the filter having a pore size of about 1 to about 10 microns;
(2) recirculating the sample through the TFF unit at a predetermined input rate and a predetermined filtration rate, the predetermined input rate at least five times the predetermined filtration rate; wherein the predetermined filtration rate is less than the unopposed filtration rate for the filter; and
(3) isolating a cell population enriched for leukocytes through the outlet centrally disposed in the portion of the cross-flow chamber opposite the filter retentate surface.

36. The method according to claim 35, wherein the enriched cell population is substantially free of non-leukocyte blood constituents.

37. The method according to claim 36, wherein the non-leukocyte blood constituents include erythrocytes.

38. The method according to claim 35, further comprising: collecting blood from a subject and preparing the sample from the blood by leukopheresis, density centrifugation, differential lysis, filtration, or preparation of a buffy coat.

39. The method according to claim 35, wherein the non-leukocyte blood constituents include plasma and platelets.

40. The method according to claim 35, wherein the leukocytes comprise monocytes.

41. The method according to claim 35, wherein the enriched cell population comprises at least about 20% leukocytes.

42. The method according to claim 35, wherein the enriched cell population comprises at least about 60% leukocytes.

43. The method according to claim 35, wherein the sample flows in a vortex motion in the cross-flow chamber.

44. The method according to claim 35, further comprising washing the enriched cell population with a wash solution.

45. The method according to claim 35, wherein the filter has a pore size of about 3 to about 5.5 microns.

* * * * *